(12) United States Patent
Schwartz et al.

(10) Patent No.: US 6,423,693 B1
(45) Date of Patent: Jul. 23, 2002

(54) GROWTH HORMONE RELEASING HORMONE EXPRESSION SYSTEM AND METHODS OF USE, INCLUDING USE IN ANIMALS

(75) Inventors: Robert J. Schwartz, Houston; Ruxandra Draghia-Akli, Houston; Xuyang Li, Lewisville, all of TX (US); Eric M. Eastman, Highland, MD (US)

(73) Assignees: Baylor College of Medicine, Houston, TX (US); Valentis, Inc., Burlingname, CA (US)

(*) Notice: Subject to any disclaimer, the term of this patent is extended or adjusted under 35 U.S.C. 154(b) by 0 days.

(21) Appl. No.: 09/122,171

(22) Filed: Jul. 24, 1998

Related U.S. Application Data
(60) Provisional application No. 60/062,608, filed on Oct. 20, 1997, and provisional application No. 60/053,609, filed on Jul. 24, 1997.

(51) Int. Cl.$^7$ .................. A61K 31/70; C12N 15/63; C12N 5/00
(52) U.S. Cl. ............... 514/44; 435/320.1; 435/325; 435/360; 435/455
(58) Field of Search .............. 800/21; 435/320.1, 435/325, 455, 360, 365.1; 536/23.5, 24.1; 514/44

(56) References Cited

U.S. PATENT DOCUMENTS

| | | | |
|---|---|---|---|
| 4,857,470 A | | 8/1989 | Cravador et al. |
| 4,897,355 A | | 1/1990 | Eppstein et al. ............ 435/325 |
| 5,298,422 A | * | 3/1994 | Schwartz et al. ......... 435/320.1 |
| 5,756,264 A | * | 5/1998 | Schwartz et al. ......... 435/320.1 |
| 5,925,564 A | * | 7/1999 | Schwartz et al. ............ 435/325 |

FOREIGN PATENT DOCUMENTS

| | | |
|---|---|---|
| EP | 0 134 085 A1 | 3/1985 |
| EP | 0 459 747 A1 | 12/1991 |
| EP | 0 509 831 A1 | 10/1992 |
| EP | 93/09236 | 5/1993 |
| WO | 93/18759 | 9/1993 |
| WO | 93/19768 | 10/1993 |
| WO | 93/23431 | 11/1993 |
| WO | 96/21470 | 7/1996 |
| WO | 96/40911 | 12/1996 |
| WO | 97/22625 | 6/1997 |
| WO | 98/24922 | 6/1998 |

OTHER PUBLICATIONS

Mumper RJ et al. Pharm Res 13:701–9, 1996.*
Rudinger, J., Characteristics of the amino acids as components of a peptide hormone sequence, "Peptide Hormones," Ed. Parsons, JA (Univ.Park Press, Baltimore), Jun. 1976, pp. 1–7.*
Clark TM et al. Pathology Oncology Research 5:3–15, 1999.*
Anderson WF. Nature 392 (Supp):25–30, 1998.*
Verma IM and Somia N. Nature 389: 239–242. 1997.*
Orkin SH and Motulsky AG. Report and Recommendations of the Panel to Assess the NIH–investment in research on gene therapy, 1995.*
Crystal RG. Science 270:404–410. 1995.*
Ledley FD Pharmaceutical Research 13, 1595–1614, 1996.*
Hammer et al., "Expression of human growth hormone–releasing factor in transgenic mice results in increased somatic growth," *Nature* 315:413–416 (1985).
Draghia–Akli et al., "Enhanced growth by ectopic expression of growth hormone–releasing hormone using an injectable myogenic vector," *Nature Biotechnology* 15:1285–1289 (1997).
Riddell, "Chromosomal Assignment of Human Sequences Encoding Arginine Vasopressin–Neurophysin II and Growth Hormone Releasing Factor," *Somatic Cell and Molecular Genetics* 11(2):189–195 (1985).
Amselem et al., "Molecular Defects in the Growth Hormone Receptor," *Acta Paediatrica Scandinavica—Supplement* 377:81–86 (1991).
Amselem et al., "Spectrum of Growth Hormone Receptor Mutations and Associated Haplotypes in Laron Syndrome," *Human Molec. Gen.* 2:355–359 (1993).
Barb et al., "Endocrine Changes in Sows Exposed to Elevated Ambient Temperature During Lactation," *Domestic Animal Endocrinology* 8:117–127 (1991).
Bergsma et al., "Delimitation and Characterization of Cis–Acting DNA Sequences Required for the Regulated Expression and Transcriptional Control of the Chicken Skeletal α–Actin Gene," *Mol. Cell. Biol.*, 6:2462–2475 (1986).
Betherat et al., "Neuroendocrine Regulation of Growth Hormone," *Eur. J. Endocrin.* 132:12–24 (1995).
Brinster et al., "Factors Affecting the Efficiency of Introducing Foreign DNA into Mice by Microinjecting Eggs," *Proc. Natl. Acad. Sci. USA* 82:4438–4442 (1958).
Cao, Wagner, Hindmarsh, Eble, & Mullis, "Isolated Growth Hormone Deficiency: Testing the Little Mouse Hypothesis in Man and Exclusion of Mutations Within the Extracellular Domain of the Growth Hormone–Releasing Hormone Receptor," *Pediatr. Res.* 38:962–966 (1995).

(List continued on next page.)

Primary Examiner—Dave T. Nguyen
Assistant Examiner—Ram R. Shukla
(74) Attorney, Agent, or Firm—Lyon & Lyon LLP

(57) ABSTRACT

Vectors which establish controlled expression of recombinant GHRH genes within tissues at certain levels. The vector includes a 5' flanking region which includes necessary sequences for expression of a nucleic acid cassette, a 3' flanking region including a 3'UTR and/or 3'NCR, and a linker which connects the 5' flanking region to a nucleic acid sequence. The linker has a position for inserting a nucleic acid cassette. The linker does not contain the coding sequence of a gene that the linker is naturally associated with. The 3' flanking region is 3' to the position for inserting the nucleic acid cassette.

26 Claims, 17 Drawing Sheets

OTHER PUBLICATIONS

Carson et al., "Regulation of Skeletal α–Actin Promoter in Young Chickens During Hypertrophy Caused by Stretch Overload," *Am. J. Physiol.* 268:C918–24 (1995).

Chang et al., "Isolation and Characterization of Six Different Chicken Actin Genes," *Mol. Cell. Biol.* 4:2498–2508 (1984).

Chow et al., "A Combination of Closely Associated Positive and Negative Cis–Acting Promoter Elements Regulates Transcription of the Skeletal α–Actin Gene," *J. Mol. & Cell. Biol.* 10:528–538 (1990).

Chow et al., "Phased cis–Acting Promoter Elements Interact at Short Distances to Direct Avian Skeletal α–Actin Gene Transcription," *PNAS* 88:1301–1305 (1991).

Cogan et al., "Heterogeneous Growth Hormone (GH)Gene Mutations in Familial GH Deficiency," *J. Clin. Endocrin. & Metab.* 76:1224–1228 (1993).

Corpas et al., "Continuous Subcutaneous Infusions of Growth Hormone (GH) Releasing Hormone 1–44 for 14 Days Increase GH and Insulin–Like Growth Factor–I Levels in Old Men," *J. Clin. Endocrin. & Metab.* 76:134–138 (1993).

Corpas et al., "Human Growth Hormone and Human Aging," *Endocrine Rev.* 14:20–39 (1993).

D'Costa A.P. et al., "The Regulation and Mechanisms of Action of Growth Hormone and Insulin–Like Growth Factor 1 During Normal Ageing," *J. Reproduction & Fertility— Suppl.* 46:87–98 (1993).

Davis et al., "Direct Gene Transfer Into Skeletal Muscle In Vivo: Factors Affecting Efficiency of Transfer and Stability of Expression," *Human Gene Therapy* 4:151–159 (1993).

Dignam et al., "Eukaryotic Gene Transcription with Purified Components," *Mol. Cell. Biol.* 10:582–598 (1983).

Doumit & Merkel, "Conditions for Isolation and Culture of Porcine Myogenic Satellite," *Tissue & Cell* 24:253–262 (1992).

Enright, W.J. et al., "Effects of Growth Hormone–Releasing Factor and(or) Thyrotropin–Releasing Hormone on Growth, Feed Efficiency, Carcass Characteristics, and Blood Hormones and Metabolites in Beef Heifers," *Journal of Animal Science* 71:2395–2405 (1993).

Enright, W.J. et al., "Growth Hormone–Releasing Factor Stimulates Milk Production and Sustains Growth Hormone Release in Holstein Cows," *Journal of Dairy Science* 69:344–351. (1986).

Esch et al., "Characterization of A 40 Residue Peptide From A Human Pancreatic Tumor with Growth Hormone Releasing Activity," *Biochem. & Biophys. Res. Comm.* 109:152–158 (1982).

Fornwald et al., "The Complete Nucleotide Sequence of the Chick a–Actin Gene and its Evolutionary Relationship to the Actin Gene Family," *Nucl. Acids Res.* 10:3861–3876 (1982).

French et al., "Analysis of a CR1 (Chicken Repeat) Sequence Flanking the 5' End of the Gene Encoding α–Skeletal Actin," *Gene (Amst.)* 88:173–180 (1990).

Hayward & Schwartz, "Sequential Expression of Chicken Actin Genes During Myogenesis," *J. Cell Biol.* 102:1484–1493 (1986).

Hu et al., "The Complete Sequence of the Mouse Skeletal α–Actin Gene Reveals Several Conserved and Inverted Repeat Sequences Outside of the Protein–Coding Region," *Mol. Cell. Biol.* 6:15–25 (1986).

Iranmanesh et al., "Age and Relative Adiposity are Specific Negative Determinants of the Frequency and Amplitude of Growth Hormone (GH) Secretory Bursts and the Half–Life of Endogenous GH in Healthy Men," *J. Clin. Endocrin. & Metab.* 73:1081–1088 (1991).

Kotzmann, H. et al., "Effect of Elevated Growth Hormone Concentrations on the Phenotype and Functions of Human Lyphocytes and Natural Killer Cells," *Neuroendocrinology* 60:618–625 (1994).

Lee et al., "BiFunctional Transcriptional Properties of YY1 in Regulating Muscle Actin and C–myc Gene Expression During Myogenesis," *J. Oncogene* 9:1047–1052 (1994).

LeRoith, D. et al., "The Effects of Growth Hormone and Insulin–Like Growth Factor I on the Immune System of Aged Female Monkeys," *Endocrinology* 137:1071–1079 (1996).

Ling et al., "Synthesis and In Vitro Bioactivity of C–Terminal Deleted Analogs of Human Growth Hormone–Releasing Factor," *Biochem. & Biophys. Res. Comm.* 123:854–861 (1984).

Low, "The Therapeutic Use of Growth–Hormone–Releasing Hormone," *J. Pediatric Endocrin.* 6:15–20 (1993).

Manak et al., "Casein Kinase II Enhances the DNA Binding Activity of Serum Response Factor," *Genes and Development* 4:955–967 (1990).

Marcus et al., "Effects of Short Term Administration of Recombinant Human Growth Hormone to Elderly People," *J. Clin. Endocrin. & Metab.* 70:519–527 (1990).

Mayo et al., "Expression–Cloning and Sequence of a cDNA Encoding Human Growth Hormone–Releasing Factor," *Nature* 306:86–88 (1983).

Mayo et al., "Gene Encoding Human Growth Hormone–Releasing Factor Precursor: Structure, Sequence, and Chromosomal Assignment," *Proc. Natl. Acad. Sci. USA* 82:63–87 (1985).

McHugh et al., "A Comprehensive Analysis of the Development and Tissue–Specific Expression of the Isoactin Multigene Family in the Rat," *Dev. Biol.* 148:442–458 (1991).

Meacham et al., "Characterization of a Noncontiguous Gene Deletion of the Growth Hormone Receptor in Laron's Syndrome," *J. Clin. Endocrin. & Metab.* 77:1379–1383 (1993).

Minty et al., "Upstream Regions of the Human Cardiac Action Gene that Modulate Its Transcription in Muscle Cells: Presence of an Evolutionary Conserved Repeated Motif," *Mol. Cell. Biol.* 6:2137–2148 (1986).

Parks et al, "Genetics of Growth Hormone Gene Expression," *Hormone Research* 40:54–61 (1993).

Parks et al., "Growth Hormone Deficiency," *Molecular Endocrinology: Basic Concepts and Clinical Correlations* (ed. Weintraub, B.D., Raven Press Ltd., ew York, 1995, p.473–490).

Petropoulos et al., "The Chicken Skeletal Muscle α–Actin Promoter Is Tissue Specific in Transgenic Mice," *Mol. Cell. Biol.* 9:3785–3792 (1989).

Salamon et al., "The Effects of Treatment with Recombinant Human Growth Hormone on Body Composition and Metabolism in Adulte with Growth Hormone Deficiency," *New Engl. J. Med.* 321:1791–1803 (1989).

Scanlon, M.F. et al.,"Regulation of Growth Hormone Secretion," *Hormone Research* 149–154 (1996).

Studier, F.W. and Moffatt, "User of Bateriophage T7 RNA Polymerase to Direct Selective High–level Expression of Cloned Genes," *J. Mol. Biol.* 189:113–130 (1986).

Tanner et al., "Modulation of Growth Hormone (GH) Secretion and GH mRNA Levels by GH–Releasing Factor, Somatostatin and Secretagogues in Cultured Bovine Adenohypophysial," *J. Endocrinol.* 125:109–115 (1990).

Taylor et al., "Nucleotide Sequence and Expression of the Human Skeletal α–Actin Gene: Evolution of Functional Regulatory Domains," Genomics. 3(4):323–36 (1988).

Thorner et al., "Extrahypothalamic Growth–Hormone–Releasing Factor (GRF) Secretion is a Rare Cause of Acromegaly: Plasma GRF Levels in 177 Acromegalic Patients," *J. Clin. Endocrin. & Metab.* 59:846–849 (1984).

Tripathy et al., "Immune Responses to Transgene–encoded Proteins Limit the Stability of Gene Expression after Injection of Replication–Defective Adenovirus Vectors," *Nature Med.* 2:545–550 (1996).

Tripathy et al., "Long Expression of Erythropoietin in the Systematic Circulation of Mice After Intramuscular Injection of a Plasmid DNA Vector," *PNAS* 93:10876–10880 (1996).

Vandekerckhove & Weber, "Chordate Muscle Actins Differ Distinctly from Invertebrate Muscle Actins," *J. Mol. Biol.* 179:391–413 (1984).

Vnencak–Jones et al., "Molecular Basis of Human Growth Hormone on Gene Deletions," *PNAS* 85:5615–5619 (1988).

Wang, Y. et al., "Ligand–Inducible and Liver–Specific Target Gene Expression in Transgenic Mice," *Nature Biotechnology* 15:239–243 (1997).

Wells, "Improved Gene Transfer by Direct Plasmid Injection Associated with Regeneration in Mouse Skeletal Muscle," *FEBS Lett.* 332:170–182 (1993).

Wolff et al., "Conditions Affecting Direct Gene Transfer into Rodent Muscle In Vivo," *BioTechniques* 11:4374–485 (1991).

Wolff et al., "Direct Gene Transfer into Mouse Muscle In Vitro," *Science* 247:1465–1468 (1990).

Wolff et al., "Long–term Persistence of Plasmid DNA and Foreign Gene Expression in Mouse Muscle," *Human Mol. Genet.* 1:363–369 (1992).

Yao et al., "Primary Myoblast–mediated Gene Transfer: Persistent Expression of Human Factor IX in Mice," *Gene Therapy* 1:99–107 (1994).

Zakut, "Nucleotide Sequence of the Rat Skeletal Muscle Actin Gene," *Nature* 298:857–859 (1982).

* cited by examiner

RESTRICTION MAP OF THE CHICKEN SKELETAL ALPHA ACTIN GENE

Codon Frequency  human_high.doc

Codon usage for human (highly expressed) genes 1/24/91

| AmAcid | Codon | Number | /1000 | Fraction | AmAcid | Codon | Number | /1000 | Fraction |
|---|---|---|---|---|---|---|---|---|---|
| Gly | GGG | 905.00 | 18.76 | 0.24 | Trp | TGG | 652.00 | 13.51 | 1.00 |
| Gly | GGA | 525.00 | 10.88 | 0.14 | End | TGA | 109.00 | 2.26 | 0.55 |
| Gly | GGT | 441.00 | 9.14 | 0.12 | Cys | TGT | 325.00 | 6.74 | 0.32 |
| Gly | GGC | 1867.00 | 38.70 | 0.50 | Cys | TGC | 706.00 | 14.63 | 0.68 |
| Glu | GAG | 2420.00 | 50.16 | 0.75 | End | TAG | 42.00 | 0.87 | 0.21 |
| Glu | GAA | 792.00 | 16.42 | 0.25 | End | TAA | 46.00 | 0.95 | 0.23 |
| Asp | GAT | 592.00 | 12.27 | 0.25 | Tyr | TAT | 360.00 | 7.46 | 0.26 |
| Asp | GAC | 1821.00 | 37.75 | 0.75 | Tyr | TAC | 1042.00 | 21.60 | 0.74 |
| Val | GTG | 1866.00 | 38.68 | 0.64 | Leu | TTG | 313.00 | 6.49 | 0.06 |
| Val | GTA | 134.00 | 2.78 | 0.05 | Leu | TTA | 76.00 | 1.58 | 0.02 |
| Val | GTT | 198.00 | 4.10 | 0.01 | Phe | TTT | 336.00 | 6.96 | 0.20 |
| Val | GTC | 728.00 | 15.09 | 0.25 | Phe | TTC | 1377.00 | 28.54 | 0.80 |
| Ala | GCG | 652.00 | 13.51 | 0.17 | Ser | TCG | 325.00 | 6.74 | 0.09 |
| Ala | GCA | 488.00 | 10.12 | 0.13 | Ser | TCA | 165.00 | 3.42 | 0.05 |
| Ala | GCT | 654.00 | 13.56 | 0.17 | Ser | TCT | 450.00 | 9.33 | 0.13 |
| Ala | GCC | 2057.00 | 42.64 | 0.53 | Ser | TCC | 958.00 | 19.86 | 0.28 |
| Arg | AGG | 512.00 | 10.61 | 0.18 | Arg | CGG | 611.00 | 12.67 | 0.21 |
| Arg | AGA | 298.00 | 6.18 | 0.10 | Arg | CGA | 183.00 | 3.79 | 0.06 |
| Ser | AGT | 354.00 | 7.34 | 0.10 | Arg | CGT | 210.00 | 4.35 | 0.07 |
| Ser | AGC | 1171.00 | 24.27 | 0.34 | Arg | CGC | 1086.00 | 22.51 | 0.37 |
| Lys | AAG | 2117.00 | 43.88 | 0.82 | Gln | CAG | 2020.00 | 41.87 | 0.88 |
| Lys | AAA | 471.00 | 9.76 | 0.18 | Gln | CAA | 283.00 | 5.87 | 0.12 |
| Asn | AAT | 314.00 | 6.51 | 0.22 | His | CAT | 234.00 | 4.85 | 0.21 |
| Asn | AAC | 1120.00 | 23.22 | 0.78 | His | CAC | 870.00 | 18.03 | 0.79 |
| Met | ATG | 1077.00 | 22.32 | 1.00 | Leu | CTG | 2864.00 | 59.78 | 0.58 |
| Ile | ATA | 88.00 | 1.82 | 0.05 | Leu | CTA | 166.00 | 3.44 | 0.03 |
| Ile | ATT | 315.00 | 6.53 | 0.18 | Leu | CTT | 238.00 | 4.93 | 0.05 |
| Ile | ATC | 1369.00 | 28.38 | 0.17 | Leu | CTC | 1276.00 | 26.45 | 0.26 |
| Thr | ACG | 405.00 | 8.40 | 0.15 | Pro | CCG | 482.00 | 9.99 | 0.17 |
| Thr | ACA | 373.00 | 7.73 | 0.14 | Pro | CCA | 456.00 | 9.45 | 0.16 |
| Thr | ACT | 358.00 | 7.42 | 0.14 | Pro | CCT | 568.00 | 11.77 | 0.19 |
| Thr | ACC | 1502.00 | 31.13 | 0.57 | Pro | CCC | 1410.00 | 29.23 | 0.48 |

Fig. 4 pRH0964 (from 539 to 766) is the wild type human GHRH sequence translate _7_9 is the GHRH sequence with optimal human codons LOCUS      pRH0964          3697 bp dsDNA       Circular
DEFINITION pVC0289 with SK-GHRH (NotI/salI) fragment from pMVG3X Quality:  1577      Length:  228      Match display thresholds for the alignment(s)
Ratio:    6.917     Gaps:    0        | = IDENTITY
Percent Similarity: 83.772   Percent Identity: 83.772       : = 5
                                                            . = 1

TOP ROW (BASES 539 TO 766)  = SEQ ID NO. 1
BOTTOM ROW (BASES 1 TO 228) = SEQ ID NO. 2

```
539  ATGGTGCTCTGGGTGTTCTTCTTTGTGATCCTCACCCTCAGCAACAGCTC  588
     ||||||||||||||||||||||||||| ||||||||| |||||||||||||
  1  ATGGTGCTGTGGGTGTTCTTCTTCGTTGATCCTGACCCTGAGCAACAGCAG   50

589  CCACTGCTCCCCACCTCCCCCCTTTGACCCTCAGGATGCGGCGGTATGCAG  638
     ||||| ||| || ||||| || |||||||||||||| ||  ||||  |||
 51  CCACTGCAGCCCCCCCCCCCCCCTGACCCCTGCGCATGCGCCGCTACGCCG  100

639  ATGCCATCTTCACCAACAGCTACCGGAAGGTGCTGGGCCAGCTGTCCGCC  688
     |||||||| ||||||||||||||||||||||||||||||||||||  |||
101  ACGCCATCTTCACCAACAGCTACCGCAAGGTGCTGGGCCAGCTGAGCGCC  150

689  CGCAAGCTGCTCCAGGACATCATGAGCAGGCAGGGAGAGAGCAACCA     738
     |||||||||||  ||||||||||||||||||||| |||||||||||||
151  CGCAAGCTGCTGCAGGACATCATGAGCCGCCAGCAGGGCGAGAGCAACCA  200

739  AGAGCGAGGAGCAAGGGCACGGCTTTAA                        766
     |||| |||||||  ||||  ||||||||
201  GGAGCGCGGCGCCCGCGCCCGCCCTGTGA                       228
```

Fig. 5 pSK-GHRH NotI/SalI fragment (SK promoter, GHRHcDNA, hGH3')
Coding region for GHRH in bold.

SEQ ID NO. 4

GGCCGCTCTT ACTGCCTGCC CCCTGCCTGG CACAGCCCGT ACCTGGCCGC ACGCTCCCTC
ACAGGTGAAG CTCGAAAACT CCGTCCCCGT AAGGAGCCCC GCTGCCCCCC GAGGCCTCCT
CCCTCACGCC TCGCTGCGCT CCCGGCTCCC GCACGGCCCT GGGAGAGGCC CCCACCGCTT
CGTCCTTAAC GGGCCCGGCG GTGCCGGGGG ATTATTTTCG GCCTCTCGGC CCGGGGGGCC
CGGCAGACGC TCCTTATACG GCCCGGCCTC GCTCACCTGG GCCGCGGCCA GGAGCGCCTT
CTTTGGGCAG CGCGGGGCCG GGGCCGCGCC GGGCCCGACA CCCAAATATG GCGACGGCCG
GGGCCGCATT CCTGGGGCC GGGCGGTGCT CCCGCCCGCC TCGATAAAAG GCTCCGGGGC
CGGCGGCGGC CCACGAGCTA CCCGGAGGAG CGGGAGGCGT CTCTGCCTAG AACTAGTGGA
TCCCAAGGCC CAACTCCCCG AACCACTCAG GTCCTGTGG ACAGCTCACC TAGCTGCCAT
GGTGCTCTGG GTGTTCTTCT TTGTGATCCT CACCCTCAGC AACAGCTCCC ACTGCTCCCC
ACCTCCCCCT TTGACCCTCA GGATGCGGCG GTATGCAGAT GCCATCTTCA CCAACAGCTA
CCGGAAGGTG CTGGGCCAGC TGTCCGCCCG CAAGCTGCTC CAGGACATCA TGAGCAGGCA
GCAGGGAGAG AGCAACCAAG AGCGAGGAGC AAGGGCACGG CTTTAATGAC TGCAGGAATT
CGATATCAAG CTTATCGAGG GTGGCATCCC TGTGACCCCT CCCCAGTGCC TCTCCTGGCC
CTGGAAGTTG CCACTCCAGT GCCCACCAGT CTATATT TAAAATTAAG TTGCATCATT
TTGTCTGACT AGGTGTCCTT ACCTGTAGGG CCTGCGGGT GGGGGGTGGT ATGGAGCAAG
GGGCCCAAGT TGGGAAGACA ACCTGTAGGG CCTGCGGGT CTATTCGGGA ACCAAGCTGG
AGTGCAGTGG CACAATCTTG GCTCACTGCA ATCTCCGCCT CCTGGGTTCA AGCGATTCTC
CTGCCTCAGC CTCCCGAGTT GTTGGGATTC CAGGCATGCA TGACCAGGCT CAGCTAATTT
TTGTTTTTTT GGTAGAGACG GGGTTTCACC ATATTGGCCA GGCTGGTCTC CAACTCCTAA
TCTCAGGTGA TCTACCCACC TTGGCCTCCC AAATTGCTGG GATTACAGGC GTGAACCACT
GCTCCCTTCC CTGTCCTTCT GATTTAAAA TAACTATACC AGCAGGAGGA CGTCCAGACA
CAGCATAGGC TACCTGCCAT GGCCCAACCG GTGGGACATT TGAGTTGCTT GCTTGGCACT
GTCCTCTCAT GCGTTGGGTC CACTCAGTAG ATGCCTGTTG AATTCAAGCT TATCGATACC
G

GROWTH HORMONE RELEASING HORMONE EXPRESSION SYSTEM AND METHODS OF USE, INCLUDING USE IN ANIMALS

STATEMENT OF RELATED APPLICATIONS

This application claims priority to U.S. patent application Ser. No. 60/062,608, filed Oct. 20, 1997 and U.S. patent application Ser. No. 60/053,609, filed Jul. 24, 1997, both of which are incorporated herein by reference in their entirety, including any drawings.

The work herein was supported by grants from the United States Government. The United States Government may have certain rights in the invention.

FIELD OF THE INVENTION

The present invention is in the field of recombinant DNA technology. This invention relates to vectors which encode stable messenger RNA (mRNA) and methods of using such vectors. In particular, this invention relates to vectors which establish controlled expression of recombinant genes within a tissue; the expression may be at levels which are useful for gene therapy and other applications. The invention further relates to vectors able to express growth hormone releasing hormone (GHRH) and gene sequences inserted into vectors that control the production of growth hormone releasing hormone in non-human vertebrate animals. The invention is directed further to the use of these vectors in the respective non-human animals to further growth and strengthen their immune systems.

BACKGROUND OF THE INVENTION

None of the information provided herein is admitted to be prior art to the present invention, but is provided only to aid the understanding of the reader.

Growth hormone (GH) secretion by the anterior pituitary is stimulated by growth hormone releasing hormone (GHRH) and inhibited by stomatostatin (SS), both hypothalamic hormones (Scanlong, M. F. et al., 1996, *Hormone Research* 149–154). GH enhances protein synthesis, lypolysis, and epiphyseal growth, and is implicated in the regulation of the immune system. GH increases circulating insulin-like growth factor I (IGF-1) levels, which in turn, mediates growth in the liver and peripheral tissues.

The GHRH-GH-IGF-I axis undergoes dramatic changes during the aging process and in the elderly (Iranmanesh et al., 1991, *J. Clin. Endocrin. & Metab.* 73:1081–1088; D'Costa A. P. et al., 1993, *J. Reproduction & Fertility*—*Suppl.* 46:87–98,) with decreased GH production rate and GH half-life, decreased IGF-I response to GH and GHRH stimuli that lead to osteoporosis, increase in fat and decrease in lean body mass and tissue function (Corpas et al., 1993, *Endocrine Rev.* 14:20–39).

In addition, genetic disorders of growth have also been ascribed to defects in the GHRH-GH-IGF-I axis, as those of GHRH receptor (Cao, Wagner, Hindmarsh, Eble, & Mullis, 1995, *Pediatr. Res.* 38:962–966), GH gene (Cogan et al., 1993, *J. Clin. Endocrin. & Metab.* 76:1224–1228; Vnencak-Jones et al., 1988, *PNAS* 85:5615–5619), GH receptor (Amselem et al., 1993, *Human Molec. Gen.* 2:355–359; Amselem et al., 1991, *Paediatrica Scandinavica—Supplement* 377:81–86; Meacham et al., 1993, *J. Clin. Endocrin. & Metab.* 77:1379–1383) and pit-1 (Parks et al, 1993, *Hormone Research* 40:54–61) a pituitary specific transcription factor. In many cases growth retardation (GR) is a secondary manifestation of an unrelated primary affection (Turner syndrome, chronic renal failure, ovary resistant syndrome) or the exact cause of GR can not be established (Parks et al., in *Molecular Endocrinology: Basic Concepts and Clinical Correlations* (ed. Weintraub, B. D., Raven Press Ltd., New York, 1995) p.473–490).

In these cases of GR where the GHRH-GH-IGF-I axis is unaffected and in elderly, as well as in nonstatural related catabolic conditions (burn, sepsis, trauma associated pathology, chronic obstructive pulmonary disease), GH or GHRH replacement therapy is efficient.

Recombinant GH therapy is currently used in clinics, but a large number of studies have shown that side effects occur frequently, including edema, hypertension, carpal tunnel syndrome, hyperinsulinemia and impaired glucose tolerance (Marcus et al., 1990, *J. Clin. Endocrin. & Metab.* 70:519–527; Salomon et al., 1989, *New Engl. J. Med.* 321:1797–1803).

GH and IGF-1 also have beneficial effects on immune function (LeRoith, D. et al., *Endocrinology* 137:1071–1079 (1996)); Kotzmann, H. et al., *Neuroendocrinology* 60:618–625 (1994)). In farm animals, GHRH is galactopoietic (stimulates milk production) with no alteration in milk composition, increases the feed to milk conversion and sustains growth, mostly through increased lean body mass (Enright, W. J. et al., *Journal of Animal Science* 71:2395–2405 (1993); Enright, W. J. et al., *Journal of Dairy Science* 69:344–351 (1986)).

Studies have shown that relatively small amounts of GHRH are required to stimulate the production and secretion of GH in all species. Some benefits of increasing GH in non-human vertebrate animals are improved growth rates, an increase in lean body mass, an increase in feed efficiency in pigs, beef cattle and sheep, increased milk production in dairy cows and goats, and enhanced production of lean meat and egg production in poultry.

GH also enhances the immune system in animals. In animals GHRH will have a great therapeutic utility in the treatment of cachexia in chronic diseases such as cancer, diabetes, due to growth hormone production abnormalities, enhancement of burn and wound healing, bone healing, retardation of the aging process and osteoporosis. However, the greatest use will be in agricultural animals. Intramuscular injection of DNA vector can persist for several months to produce sustained levels of GHRH. The intramuscular delivery of GHRH vector represents a practical method for improving performance in livestock animals.

Current limitations of recombinant GHRH therapy are the high cost of recombinant proteins, the short half-life of the peptides in vivo and the requirement for frequent administration (1–3 times/day) of either subcutaneous or intravenous injections. Using a GHRH injectable DNA plasmid based vector will enhance endogenous GH secretion in vertebrate animals with GH deficiencies in a manner more closely mimicking the natural process and in a less expensive manner than classical therapies.

SUMMARY OF THE INVENTION

The present invention is based in part on the identification of certain nucleic acid sequences which confer advantageous tissue targeting, expression, and secretion properties. Such sequences are utilized in the construction of plasmid vectors encoding GHRH, for delivery and expression of the GHRH coding sequences.

Expression of these vectors can be tissue specific. These vectors are useful in facilitating enhanced expression in tissues as well as in targeting expression with tissue specificity. These vectors can be used to treat diseases by gene therapy by restricting expression of a gene encoded on the vector to targeted tissues. Vectors containing such sequences are able to provide gene delivery and controlled expression of recombinant genes within tissues; such expression can be at levels that are useful for gene therapy and other applications. These vectors can also be used to create transgenic animals for research or livestock improvement.

The ability of the expression vector to provide enhanced product secretion as well as direct expression to specific tissues allows the vector to be used for treating numerous diseases. The above vectors can be used in gene therapy where a vector encoding a therapeutic product is introduced into a tissue so that the tissue will express the therapeutic product. For example, the above vectors may be used for treating muscle atrophy associated with neurological, muscular, or systemic disease or aging by causing tissues to express certain trophic factors.

In addition, the vectors can be used for gene replacement of inherited genetic defects or acquired hormone deficiencies, for vaccination in humans or animals to induce immune responses, or for creating transgenic animals. The transgenic animals can be used as models for studying human diseases, for assessing and exploring novel therapeutic methods, to assess the effects of chemical and physical carcinogens, and to study the effect of various genes and genetic regulatory elements. Furthermore, transgenic animals can be used to develop commercially important livestock species. The above vectors can also be used to transform cells to produce particular proteins and RNA in vitro.

Expression of such vectors having a GHRH encoding sequence in the body of a vertebrate, e.g., a human, can produce both direct and indirect effects. The GHRH produces direct effects by the direct action of the GHRH polypeptide. However, indirect effects may also be produced due to the effect of the GHRH inducing or turning on the expression of other genes, or modulating the activity of other gene products. In particular, expression of GHRH can affect the levels of GH and IGF-I.

In a first aspect, the present invention features a vector for expression of a nucleic acid sequence in tissue by encoding stable mRNA. The vector includes a 5' flanking region which includes necessary sequences for the expression of a nucleic acid cassette, which include a promoter sequence, preferably an actin gene promoter sequence, more preferably a skeletal actin gene. The vector also includes a 3' flanking region, which includes a 3'UTR and/or a 3'NCR, which enhances secretion of the product expressed from the nucleic acid cassette. Preferably the 3'UTR is from the 3' region of a growth hormone gene, more preferably from a human growth hormone gene. Alternatively, in related vectors, the 3' sequences may be selected to provide a higher level of retention of the product within a tissue, e.g., within a muscle tissue, rather than enhancing secretion. Such sequences can, for example, be from a skeletal α-actin gene. The vector also includes a linker which connects the 5' flanking region to a nucleic acid. The linker does not contain the coding sequence of a gene that the linker is naturally associated with. That is, the linker is not the normal gene associated with the 5' and 3' regions. Preferably, the linker includes a sequence coding for a GHRH gene, more preferably human GHRH. The 3' flanking region is 3' to the position for inserting coding sequence or the nucleic acid cassette.

The term "flanking region" as used herein refers to nucleotide sequences on either side of an associated gene.

Flanking regions can be either 3' or 5' to a particular gene in question. In general, flanking sequences contain elements necessary for regulation of expression of a particular gene. Such elements include, but are not limited to, sequences necessary for efficient expression, as well as tissue specific expression. Examples of sequences necessary for efficient expression can include specific regulatory sequences or elements adjacent to or within the protein coding regions of DNA. These elements, located adjacent to the gene, are termed cis-acting elements. The signals are recognized by other diffusible biomolecules in trans to alter the transcriptional activity. These biomolecules are termed trans-acting factors. Trans-acting factors and cis-acting elements have been shown to contribute to the timing and developmental expression pattern of a gene. Cis-acting elements are usually thought of as those that regulate transcription and are usually found within promoter regions and within upstream (5') or downstream (3') DNA flanking regions.

Flanking DNA with regulatory elements that regulate expression of genes in tissue may also include modulatory or regulatory sequences which are regulated by specific factors, such as glucocorticoids, androgens, progestins, anti-progestins (PCT US93/04399; PCT US96/04324), vitamin $D_3$ and its metabolites, vitamin A and its metabolites, retinoic acid, calcium as well as others.

"Modulatory" or "regulatory" sequences as used herein refer to sequences which may be in the 3' or 5' flanking region, where such sequences can enhance activation and/or suppression of the transcription of the associated gene.

"Responsive" or "respond" as used herein refers to the enhancement of activation and/or suppression of gene transcription as discussed below.

"Metabolite" as used herein refers to any product from the metabolism of the regulatory factors which Ace regulate gene expression.

In addition to the above, either or both of the 3' or 5' flanking regions can cause tissue specificity. Such tissue specificity provides expression predominantly in a specified cell or tissue.

"Predominantly" as used herein means that the gene associated with the 3' or 5' flanking region is expressed to a higher degree only in the specific tissue as compared to low expression or lack of expression in nonspecific tissue. The 3' or 5' flanking regions singularly or together as used herein may provide expression of the associated gene in other tissues but to a lower degree than expression in tissues or cells where expression is predominate. Expression is preferentially in the specified tissue. Such predominant expression can be compared with the same magnitude of difference as will be found in the natural expression of the gene (i.e. as found in a cell in vivo) in that particular tissue or cell type as compared with other nonspecific tissues or cells. Such differences can be observed by analysis of mRNA levels or expression of natural gene products, recombinant gene products, or reporter genes. Furthermore, northern analysis, X gal immunofluorescence or CAT assays as discussed herein and as known in the art can be used to detect such differences.

The 3' flanking region contains sequences or regions, e.g. 3'UTR and/or 3' NCR, which regulate expression of a nucleic acid sequence with which it is associated. The 3' flanking regions can provide tissue-specific expression to an associated gene. The 3' flanking region also contains a transcriptional termination signal.

The term "3' flanking region" as used herein includes that portion of a naturally occurring sequence 3' to the transcribed portion of the gene which are responsible for mRNA processing and/or tissue-specific expression. That portion can be readily defined by known procedures. For example, the portions of a 3' flanking region which are responsible for mRNA stability and/or tissue-specific expression can be mapped by mutational analysis or various clones created to define the desired 3' flanking region activity in a selected vector system.

The 3' flanking region can contain a 3'UTR and/or a 3' NCR. The term "3' untranslated region" or "3'UTR"refers to the sequence at the 3' end of structural gene which is transcribed from the DNA but not translated into protein. This 3'UTR region does not contain a poly(A) sequence, but generally contains a site at which a poly(A) sequence is added. Poly (A) sequences are only added after the transcriptional process.

Myogenic-specific 3'UTR sequences can be used to allow for specific stability in muscle cells or other tissues. As described below, myogenic-specific sequences refers to gene sequences normally expressed in muscle cells, e.g., skeletal, heart and smooth muscle cells. Myogenic specific mRNA stability provides an increase in mRNA stability within myogenic cells. The increase in stability provides increased expression. The 3'UTR and 3'NCR sequences singularly or together can provide a higher level of mRNA accumulation through increased mRNA stability. Thus, increased expression and/or stability of mRNA leads to increased levels of protein production.

The term "3' non-coding region" or "3'NCR" is a region which is adjacent to the 3'UTR region of a structural gene. The 3'NCR region generally contains a transcription termination signal. Once transcription occurs and prior to translation, the RNA sequence encoded by the 3'NCR is usually removed so that the poly(A) sequence can be added to the mRNA. The 3'NCR sequences can also be used to allow mRNA stability as described above. The 3'NCR may also increase the transcription rate of the nucleic acid cassette.

Either or both of the 3'UTR and 3'NCR sequences can be selected from a group of myogenic-specific genes. Examples of myogenic-specific genes include the skeletal α-actin gene, fast myosin-light chain 1/3 gene, myosin-heavy chain gene, troponin T gene, acetylcholine receptor subunit genes and muscle creatinine kinase gene.

In reference to 3' flanking regions of this invention, the term "growth hormone" refers to a gene product identified as a growth hormone, for example, human growth hormone or bovine growth hormone. Homologous gene sequences are known in the art for a variety of different vertebrate animals. In different embodiments, the vectors can incorporate 3' sequences, including 3'UTR sequences from such growth hormone genes. The 3' sequence can be modified from the sequence naturally found in the animal, for example by the deletion of ALU repeat sequence from human growth hormone 3'UTR. The deletion of ALU repeats or ALU repeat-like sequences can be performed with a variety of 3' sequences; such deletion generally reduces the rate of homologous recombination. A variety of other modifications may also be made without destroying the tissue targeting, stabilizing, and secretion properties of the 3' sequence.

The 5' flanking region is located 5' to the associated gene or nucleic acid sequence to be expressed. As with the 3' flanking region, the 5' flanking region can be defined by known procedures. For example, the active portion of the 5' flanking region can be mapped by mutational analysis or various clones of the 5' flanking region created to define the desired activity in a selected vector. The 5' flanking region can include, in addition to the above regulatory sequences or elements, a promoter, a TATA box, and a CAP site, which are in an appropriate relationship sequentially and positionally for the expression of an associated gene.

In this invention, "sequences necessary for expression" are those elements of the 5' flanking region which are sequentially and positionally in an appropriate relationship to cause controlled expression of a gene within a nucleic acid cassette. Expression is controlled to certain levels within tissues such that the expressed gene is useful for gene therapy and other applications involving gene delivery. The 5' sequence can contain elements which regulate tissue-specific expression or can include portions of a naturally occurring 5' element responsible for tissue-specific expression.

The term "promoter," as used herein refers to a recognition site on a strand of DNA to which RNA polymerase binds. The promoter usually is a DNA fragment of about 100 to about 200 base pairs (in eukaryotic genes) in the 5' flanking DNA upstream of the CAP site or the transcriptional initiation start site. The promoter forms an "initiation complex" with RNA polymerase to initiate and drive transcriptional activity. The complex can be modified by activating sequences termed "enhancers" or inhibitory sequences termed "silencers". The promoter can be one which is naturally (i.e., associated as if it were within a cell in vivo) or non-naturally associated with a 5' flanking region.

A variety of promoters can be used. Some examples include thymidine kinase promoter, myogenic-specific promoters including skeletal α-actin gene promoter, fast myosin light chain 1 promoter, myosin heavy chain promoter, troponin T promoter, and muscle creatinine kinase promoter, as well as non-specific promoters including the cytomegalovirus immediate early promoter, and Rous Sarcoma virus LTR. These promoters or other promoters used with the present invention can be mutated in order to increase expression of the associated gene. Furthermore a promoter may be used by itself or in combination with elements from other promoters, as well as various enhancers, transcript stabilizers, or other sequences capable of enhancing function of the vector.

"Mutation" as used herein refers to a change in the sequence of genetic material from normal, causing a change in the functional characteristics of the gene. This includes gene mutations where only a single base is changed in the natural gene promoter sequences or multiple bases are changed.

The term "intron" as used herein refers to a section of DNA occurring in a transcribed portion of a gene which is included in a precursor RNA but is then excised during processing of the transcribed RNA before translation occurs. Intron sequences are therefore not found in mRNA nor translated into protein. The term "exon" as used herein refers to a portion of a gene that is included in a transcript of a gene and survives processing of the RNA in the cell to become part of a mature mRNA. Exons generally encode three distinct functional regions of the RNA transcript. The first, located at the 5' end which is not translated into protein, termed the 5' untranslated region (5'UTR), signals the beginning of RNA transcription and contains sequences that direct the mRNA to the ribosomes and cause the mRNA to be bound by ribosomes so that protein synthesis can occur. The second contains the information that can be translated into the amino acid sequence of the protein or function as a bioactive RNA molecule. The third, located at the 3' end is not translated into protein, i.e. 3'UTR, contains the signals for termination of translation and for the addition of a polyadenylation tail (poly(A). In particular, the 3'UTR as defined above can provide mRNA stability. The intron/exon boundary will be that portion in a particular gene where an intron section connects to an exon section. The terms "TATA box" and "CAP site" are used as they are recognized in the art.

The term "linker" as used herein refers to DNA which contains the recognition site for a specific restriction endonuclease. Linkers may be ligated to the ends of DNA fragments prepared by cleavage with some other enzyme. In particular, the linker provides a recognition site for inserting the nucleic acid cassette which contains a specific nucleic sequence to be expressed. This recognition site may be but is not limited to an endonuclease site in the linker, such as Cla-I, Not-I, Xmal, Bgl-II, Pac-I, Xhol, Nhel, Sfi-I. A linker can be designed so that the unique restriction endonuclease site contains a start codon (e.g. AUG) or stop codon (e.g. TAA, TGA, TCA) and these critical codons are reconstituted when a sequence encoding a protein is ligated into the linker. Such linkers commonly include an NcoI or SphI site.

The term "leader" as used herein refers to a DNA sequence at the 5' end of a structural gene which is transcribed and translated along with the gene. The leader usually results in the protein having an n-terminal peptide extension sometimes called a pro-sequence. For proteins destined for either secretion to the extracellular medium or the membrane, this signal sequence directs the protein into endoplasmic reticulum from which it is discharged to the appropriate destination. The leader sequence normally is encoded by the desired nucleic acid, synthetically derived or isolated from a different gene sequence. A variety of leader sequences from different proteins can be used in the vectors of the present invention. Some non-limiting examples include gelsolin, albumin, fibrinogen and other secreted serum proteins.

The term "vector" as used herein refers to a nucleic acid, e.g., DNA derived from a plasmid, cosmid, phasmid or bacteriophage or synthesized by chemical or enzymatic means, into which one or more fragments of nucleic acid may be inserted or cloned which encode for particular genes. The vector can contain one or more unique restriction sites for this purpose, and may be capable of autonomous replication in a defined host or organism such that the cloned sequence is reproduced. The vector may have a linear, circular, or supercoiled configuration and may be complexed with other vectors or other materials for certain purposes. The components of a vector can include but are not limited to a DNA molecule incorporating: (1) a sequence encoding a therapeutic or desired product; and (2) regulatory elements for transcription, translation, RNA stability and replication.

The vector can be used to provide expression of a nucleic acid sequence in tissue. In the present invention this expression is enhanced by providing stability to an mRNA transcript from the nucleic acid sequence and/or secretion of the therapeutic protein. Expression includes the efficient transcription of an inserted gene or nucleic acid sequence within the vector. Expression products may be proteins including but not limited to pure protein (polypeptide), glycoprotein, lipoprotein, phosphoprotein, or nucleoprotein. Expression products may also be RNA. The nucleic acid sequence is contained in a nucleic acid cassette. Expression of the nucleic acid can be continuous or controlled by endogenous or exogenous stimuli.

The term "control" or "controlled" as used herein relates to the expression of gene products (protein or RNA) at sufficiently high levels such that a therapeutic effect is obtained. Levels that are sufficient for therapeutic effect are lower than the toxic levels. Levels of expression for therapeutic effect within selected tissues corresponds to reproducible kinetics of uptake, elimination from cell, post-translational processing, and levels of gene expression, and, in certain instances, regulated expression in response to certain endogenous or exogenous stimuli (e.g., hormones, drugs).

The term "nucleic acid cassette" as used herein refers to the genetic material of interest which codes for a protein or RNA. The nucleic acid cassette is positionally and sequentially oriented within the vector such that the nucleic acid in the cassette can be transcribed into RNA, and when necessary, translated into a protein in the transformed tissue or cell. Preferably, the cassette has 3' and 5' ends adapted for ready insertion into a vector, e.g., it has restriction endonuclease sites at each end. In the vectors of this invention, a nucleic acid cassette contains a sequence coding for growth hormone releasing hormone (GHRH), e.g., human GHRH.

The term "tissue" as used herein refers to a collection of cells specialized to perform a particular function or can include a single cell. The cells may be of the same type or of different types.

The term "gene", e.g., "myogenic genes," as used herein refers to those genes exemplified herein and their equivalence in other animal species or other tissues. Homologous sequences (i.e. sequences having a common evolutionary origin representing members of the same superfamily) or analogous sequences (i.e. sequences having common properties though a distinct evolutionary origin) are also included so long as they provide equivalent properties to those described herein. It is important in this invention that the chosen sequence provide the enhanced levels of expression, expression of the appropriate product, and/or tissue-specific expression as noted herein. Those in the art will recognize that the minimum sequences required for such functions are encompassed by the above definition. These minimum sequences are readily determined by standard techniques exemplified herein.

The term "myogenic" refers to muscle tissue or cells. The muscle tissue or cells can be in vivo, in vitro, or in vitro tissue culture and capable of differentiating into muscle tissue. Myogenic cells include skeletal, heart and smooth muscle cells. Genes are termed "myogenic" or "myogenic-specific" if they are expressed or expressed preferentially in myogenic cells. Vectors are termed "myogenic" or "myogenic-specific" if they function preferentially in myogenic muscle tissue or cells. Myogenic activity of vectors can be determined by transfection of these vectors into myogenic cells in culture, injected into intact muscle tissue, or injected into mammalian oocytes to be stably incorporated into the genome to generate transgenic animals which express the protein or RNA of interest in myogenic cells.

The term "non-myogenic" refers to tissue or cells other than muscle. The tissues or cells can be in vivo, in vitro, or in vitro tissue culture.

In a preferred embodiment, the vector described above may have its 5' flanking region from myogenic genes, in particular the skeletal α-actin gene, e.g., a chicken skeletal α-actin gene. Specifically, this can include a promoter sequence which may be linked with other 5'UTR sequences, which can include an intron. While vectors using the chicken skeletal α-actin promoter and/or other 5' flanking sequences are exemplified herein, the 5' sequences for α-actin genes are highly conserved, therefore, such 5' α-actin sequences can be utilized from other vertebrate species, including, for example, human.

In preferred embodiments, the 3'UTR is from a growth hormone gene, preferably from a human growth hormone gene, and preferably includes a poly(A) signal. This sequence can be linked immediately following the natural translation termination codon for a cDNA sequence coding for the protein or RNA to be expressed. As discussed above, these regions can be further and more precisely defined by routine methodology, e.g., deletion or mutation analysis or their equivalents.

The 5' or 3' sequences may have a sequence identical to the sequence as naturally found, but may also have changed sequences which provide equivalent function to a vector in which such 5' or 3' sequences are incorporated. Such a change, for example, could be a change of ten nucleotides in any of the above regions. In particular, such changes can include the deletion of ALU repeat sequences from the 3'UTR. This is only an example and is non-limiting.

Also in preferred embodiments, the sequence encoding GHRH is a synthetic GHRH coding sequence. Such a synthetic sequence has a nucleotide sequence which differs from a natural human GHRH coding sequence. It is preferred that the sequence utilize optimal codon usage; preferably at least 50%, 70%, or 90% of the codons are optimized. Thus, in preferred embodiments the synthetic DNA sequence has at least 80, 90, 95, or 99% sequence identity to the sequence of SEQ ID NO. 1. In a particular preferred embodiment, the synthetic DNA sequence has at least 95% identity, more preferably at least 99% identity, and most preferably 100% identity to the sequence of SEQ ID NO. 2.

In addition, another embodiment of the above vector may contain a regulatory system for regulating expression of the nucleic acid cassette. The term "regulatory system" as used herein refers to cis-acting or trans-acting sequences incorporated into the above vectors which regulate in some characteristic the expression of the nucleic acid of interest as well as trans-acting gene products which are co-expressed in the cell with the above described vector. Regulatory systems can be used for up-regulation or down regulation of expression from the normal levels of expression or existing levels of expression at the time of regulation. The system contributes to the timing and developmental expression pattern of the nucleic acid.

One construction of a regulatory system includes a chimeric trans-acting regulatory factor incorporating elements of a serum response factor capable of regulating expression of the vector in a cell. The chimeric transacting regulatory factor is constructed by replacing the normal DNA binding domain sequence of the serum response factor with a DNA binding domain sequence of a receptor. The serum response factor has a trans-activation domain which is unchanged. The trans-activation domain is capable of activating transcription when an agent or ligand specific to the receptor binding site binds to the receptor. Thus, regulation can be controlled by controlling the amount of the agent.

The DNA binding domain sequence of a receptor, incorporated into the chimeric trans-activating regulatory factor, can be selected from a variety of receptor groups including but not limited to vitamin, steroid, thyroid, orphan hormone, retinoic acid, thyroxine, or GAL4 receptors. The chimeric trans-activating regulator factor is usually located within the sequence of the promoter. In one preferred embodiment the promoter used in the vector is the □-actin promoter and the receptor is the vitamin D receptor.

"Receptor" as used herein includes natural receptors (i.e., as found in a cell in vivo) as well as anything that binds alike and causes compartmentalization changes in a cell.

Another embodiment of the regulatory system includes the construction of a vector with two functional units. One functional unit expresses a receptor. This functional unit contains elements required for expression including a promoter, a nucleic acid sequence coding for the receptor, and a 3'UTR and/or a 3'NCR. The second functional unit expresses GHRH or a derivative or RNA and contains, in addition, a response element corresponding to the receptor, a promoter, a nucleic acid cassette, and a 3'UTR and/or a 3'NCR. These functional units can be in the same or separate vectors.

The first functional unit expresses the receptor. It is favorable to use a receptor not found in high levels in the target tissue. The receptor forms an interaction, e.g., ionic, non-ionic, hydrophobic, H-bonding, with the response element on the second functional unit prior to, concurrent with, or after the binding of the agent or ligand to the receptor. This interaction allows the regulation of the nucleic acid cassette expression. The receptor can be from the same nonlimiting group as disclosed above. Furthermore, the vector can be myogenic specific by using myogenic specific 3'UTR and/or 3'NCR sequences.

In an exemplary preferred embodiment the plasmid can be pSK-GHRH or a plasmid comprising a nucleotide sequence which is the same as the sequence of pSK-GHRH. This is only an example and is meant to be non-limiting. Thus, sequence changes or variations can be made to one or more of the sequence elements, such as the 5' and 3' flanking regions.

In this context, the word "same" means that the sequences are functionally equivalent and have a high degree of sequence identity. However, the sequences may have a low level of sequence differences, such as by substitution, deletion, or addition of one or more nucleotides. Such sequences will preferably be less than 10%, more preferably less than 5%, and still more preferably less than 1% of the total sequence.

In particular embodiments, the vectors of the above aspect may alternatively comprise, consist essentially of, or consist of the stated elements or sequences.

A related aspect of the invention provides a formulation for delivery and expression of a GHRH gene in a cell, preferably a human GHRH gene. The formulation includes a vector of the above aspect together with one or more other components which can, for example, act to stabilize the vector or to enhance transfection efficiency, but can also provide other functions. In a preferred embodiment, the formulation includes the vector in a solution having between about 0.5% and 50% polyvinyl pyrrolidone (PVP), preferably about 5% PVP. Preferably, the PVP has a weight average molecular weight of about 50,000 g/mol. Further information is disclosed in PCT US95/17038. However, another example of a formulation includes the vector with a cationic lipid (e.g., as described in U.S. Pat. No. 4,897,355, issued Jan. 30, 1990), and can also include a co-lipid, such as a neutral co-lipid, e.g., cholesterol.

In reference to the formulations of this invention, the term "about" indicates that in preferred embodiments, the actual value for a particular parameter is in the range of 50%–200% of the stated value.

Another related aspect of the invention features a transgenic animal, at least some cells of which contain vectors of the first aspect of the present invention. These cells include germ or somatic cells. The transgenic animals can be used as models for studying human diseases, for assessing and exploring novel therapeutic methods, to assess the effects of chemical and physical carcinogens, and to study the effect of various genes and genetic regulatory elements. In addition, transgenic animals can be used to develop commercially important livestock species.

A fourth related aspect of the present invention features cells transformed with a vector of the present invention for expression of a GHRH nucleic acid sequence, preferably a human hGHRH (hGHRH) nucleic acid sequence.

As used herein, "transformation" is the change in a cell's phenotypic characteristics by the action of a gene expressing a gene product. The gene causing the phenotypic characteristic change has been transfected into the cell.

The term "transfection" as used herein refers to a mechanism of gene transfer which involves the uptake of DNA by a cell or organism. Following entry into the cell, the transforming DNA may recombine with that of the host by physically integrating into the chromosomes of the host cell, may be maintained transiently as an episomal element without being replicated, or may replicate independently as a plasmid. Preferably the transforming DNA does not integrate.

Transfection can be performed by in vivo techniques as described below, or by ex vivo techniques in which cells are co-transfected with a vector containing a selectable marker. This selectable marker is used to select those cells which have become transformed. It is well known to those skilled in the art the type of selectable markers to be used with transfection/transformation studies. An example of such a marker is a neo gene, providing neomycin/kanamycin resistance.

Transfection/transformation can be tissue-specific, i.e., involve the use of myogenic specific vectors which cause expression of the nucleic acid cassette predominantly in the tissue of choice. In particular, tissue specificity can be directed to myogenic cells by using a promoter and/or 3'UTR and/or 3'NCR sequences specific for myogenic tissue expression.

A fifth related aspect of the present invention features methods for transfecting a cell with the vectors of the present invention. These methods comprise the steps of contacting a cell in situ with a vector of the present invention for sufficient time to transfect the cell. As discussed above, transfection can be in vivo or ex vivo.

A sixth related aspect of the invention provides a method for delivery and expression of a GHRH gene, preferably a hGHRH gene. The method comprises transfecting a plurality of cells with a vector of the first aspect and incubating the cells under conditions allowing expression of a nucleic acid sequence of the vector, which codes for GHRH. The "conditions allowing expression" may be any of a variety of conditions, including in vivo and in vitro conditions. Under such conditions, the cells will produce the gene product from the vector DNA in detectable quantities.

A seventh related aspect of the present invention features a method for treating a disease or condition by transfecting cells with the above-referenced vectors. Such disease or condition may, for example, be localized or systemic. These vectors contain nucleic acid sequences coding for growth hormone releasing hormone. Diseases and conditions can include but are not limited to burn, sepsis, trauma associated pathology, chronic obstructive pulmonary disease, aging associated osteoporosis, atherogenesis, atherosclerotic cardiovascular, cerebrovascular, or peripheral vascular disease, growth disorders and hemophilia.

The muscle atrophy to be treated may be due to any of a variety of different causes. For example, muscle weakness may be primarily due to disuse atrophy which commonly occurs in situations such as joint replacement, to muscle wasting during ageing, or to disease related cachexia. The causes may also include genetic causes of muscular atrophy, including, for example, muscular dystrophy. These causes and conditions are only exemplary and are not limiting to the invention.

Thus, "localized" disease or condition refers to those in which there is specific nerve or muscle damage or atrophy to a defined and limited area of the body. A specific example is disuse atrophy. A "systemic" disease or condition refers to those which relate to the entire organism, or is widely distributed at a number of locations within the body. Examples include growth disorders, neuropathies, and muscular dystrophy.

The methods of treating disease of the present invention feature methods for establishing expression of GHRH in tissue by administration of a vector. These methods of use of the above-referenced vectors comprise the steps of administering an effective amount of the vectors to a human, animal or tissue culture.

The term "administering" or "administration" as used herein refers to the route of introduction of a vector or carrier of DNA into the body. The vectors of the above methods and the methods discussed below may be administered by various routes. In particular a preferred target cell for treatment is the skeletal muscle cell.

The term "skeletal muscle" as used herein refers to those cells which comprise the bulk of the body's musculature, i.e., striated muscle.

Administration can be directly to a target tissue or may involve targeted delivery after systemic administration. The preferred embodiments are by direct injection into muscle or targeted uptake into muscle after intra-venous injection.

The term "delivery" refers to the process by which the vector comes into contact with the preferred target cell after administration. Administration may involve needle injection into cells, tissues, fluid spaces, or blood vessels, electroporation, transfection, hypospray, iontophoresis, particle bombardment, or transplantation of cells genetically modified ex vivo. Examples of administration include intravenous, intramuscular, aerosol, oral, topical, systemic, ocular, intraperitoneal and/or intrathecal.

The preferred means for administration of vectors described above involves the use of formulations for delivery to the target cell in which the vector is associated with elements such as lipids, proteins, carbohydrates, synthetic organic compounds, or inorganic compounds which enhance the entry of the vector into the nucleus of the target cell where gene expression may occur. A particular example is polyvinyl pyrrolidone(PVP).

The term "formulation" as used herein refers to non-genetic material combined with the vector in a solution, suspension, or colloid which enhances the delivery of the vector to a tissue, uptake by cells within the tissue, intracellular trafficking through the membrane, endosome or cytoplasm into the nucleus, the stability of the vector in extracellular or intracellular compartments, and/or expression of genetic material by the cell.

In a preferred embodiment of the present invention the vector and formulation comprises a nanoparticle which is administered as a suspension or colloid. The formulation can include lipids, proteins, carbohydrates, synthetic organic compounds, or inorganic compounds. Examples of elements which are included in a formulation are lipids capable of forming liposomes, cationic lipids, hydrophilic polymers, polycations (e.g. protamine, polybrine, spermidine, polylysine), peptide or synthetic ligand recognizing receptors on the surface of the target cells, peptide or synthetic ligand capable of inducing endosomal-lysis, peptide or synthetic ligand acapable of targeting materials to the nucleus, gels, slow release matrices, salts, carbohydrates, nutrients, or soluble or insoluble particles as well as analogues or derivatives of such elements. This includes formulation elements enhancing the delivery, uptake, stability, and/or expression of genetic material into cells. This list is included for illustration only and is not intended to be limiting in any way.

Another embodiment of the present invention features the above vectors with coating elements that enhance expression as well as uptake by the cell. The term "coating" as used herein refers to elements, proteins or molecules used to associate with the vector in order to enhance cellular uptake. In particular, coating includes a DNA initiation complex and histones. The coating improves the stability of the vector, its entry into the nucleus, and the efficiency of transcription.

The term "DNA initiation complex" as used herein refers to a complex containing a serum response factor, a transcription initiation factor and a trans-regulatory factor. The serum response factor is attached to or interacts with the serum response element within the promoter region of the vector. The transcription initiation factor and the trans-regulatory factor then interact with the serum response factor and the promoter, in particular the TATA box within the promoter, to form a stable DNA complex. The term "histone" as used herein refers to nuclear proteins which associate with and/or bind to DNA, e.g., a vector. The histones can bind specifically or non-specifically to the DNA.

The term "effective amount" as used herein refers to sufficient vector administered to humans, animals or into tissue culture to produce the adequate levels of protein or RNA. One skilled in the art recognizes that the adequate level of protein or RNA will depend on the use of the particular vector. These levels will be different depending on the type of administration and treatment or vaccination.

The methods for treating diseases as disclosed herein includes treatment with biological products (specifically proteins as defined above) in which the disease being treated requires the protein to circulate through the body from the general circulation. For example, disorders which might be treated by the present invention include osteoporosis by expression of GHRH or its binding proteins. The selection of the appropriate protein to treat various diseases will be apparent to one skilled in the art.

In treating disease, the present invention provides a means for achieving: (1) sufficiently high levels of a particular protein to obtain a therapeutic effect; (2) controlled expression of product at levels which are sufficient for therapeutic effect and lower than the toxic levels; (3) controlled expression in certain tissues in order to obtain reproducible pharmacokinetics and levels of gene expression; and (4) delivery using clinically and pharmaceutically acceptable means of administration and formulation rather than transplantation of genetically engineered and selected cells.

In doing so, the present invention provides significant advances over the art. First, promoters from viral genomes and viral vectors which were used to obtain high level expression in tissue, were not able to provide controlled expression. Second, promoters from various tissue-specific genes which were used to obtain controlled expression in transgenic animals and animal models of gene therapy did not have a sufficiently high level of expression to obtain therapeutic effect. In addition, in treating diseases with the present invention, the ability to raise antibodies against protein products does not reflect the ability to achieve controlled expression of proteins within the therapeutic range.

An eighth related aspect of the present invention features a method of gene replacement for inherited genetic diseases of muscle. This method includes the transfection of muscle cells with the above-referenced vectors.

The genetic material which is incorporated into the cells from the above vectors can be any natural or synthetic nucleic acid. For example, the nucleic acid can be: (1) not normally found in the tissue of the cells; (2) normally found in a specific tissue but not expressed at physiological significant levels; (3) normally found in specific tissue and normally expressed at physiological desired levels; (4) any other nucleic acid which can be modified for expression in skeletal muscle cells; and (5) any combination of the above. In addition to the genetic material which is incorporated into tissue, the above reference is also applicable to genetic material which is incorporated into a cell.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The present invention also concerns a gene therapy approach in which a species-specific GHRH cDNA plasmid based expression vector or other species-specific GHRH expression vectors are targeted into peripheral organs and expressed by the transfected cells. The species-specific GHRH polypeptide is then processed, secreted and transported to the anterior pituitary, where it stimulates GH release.

As used herein, a "plasmid" is an extrachromosomal genetic element consisting of a circular duplex of DNA which can replicate independently of chromosomal DNA. Plasmids are used in gene transfer, as the vehicle by means of which DNA fragments can be introduced into a host organism, and are associated with the transfer of antibiotic resistance.

The present invention concerns a method of expressing growth hormone releasing hormone (GHRH) in a non-human vertebrate animal comprising the step of inserting a DNA carrier vehicle containing a gene sequence encoding a growth hormone releasing hormone polypeptide sequence operatively linked to a vertebrate gene promoter into said non-human vertebrate animal tissue under conditions where said gene (a segment of DNA which codes for a specific polypeptide or RNA molecule) is expressed and produces hormone releasing hormone.

The term "non-human vertebrate animal" encompasses all animals having a backbone or spinal column, except for human beings. Vertebrate animals include fishes, amphibians, reptiles, birds and mammals.

As used herein, a "DNA carrier vehicle" refers to some means by which DNA fragments can be introduced into a host organism or host tissue. The DNA carrier vehicle may be designed to incorporate the gene of interest and any accessory genetic sequences.

The "gene sequence" preferably is a nucleic acid molecule.

The present invention concerns gene sequences that encode for a growth hormone releasing hormone having one of the following sequences; SEQ ID NO.5, SEQ ID NO.6, SEQ ID NO.7, SEQ ID NO.8, SEQ ID NO.9, or SEQ ID NO.11; or where the non-human vertebrate animal is one of the following species; porcine, bovine, equine, canine, feline, caprine, avian (chicken, turkey, duck), ovine or fish.

The present invention also can involve GHRH gene sequence in the DNA carrier vehicle that contain no intervening sequences in the GHRH region.

A further object of the invention is use of a DNA carrier vehicle in which the promoter is from a skeletal α-actin gene.

The present invention includes a DNA carrier vehicle which is injected into said animal muscle.

The present invention includes a plasmid DNA vector, adenovirus or adeno-associated virus as DNA carrier vehicles capable of infecting non-human vertebrate animals in various tissues.

The present invention can include a DNA carrier vehicle in which the promoter-GHRHcDNA-3'UTR is incorporated into an adeno-associated virus. The present invention can additionally include an embodiment where the vectors encode for an Arg—Arg sequence before a tyrosine or a histidine.

A further object of the invention is incorporation of a gene switch sequence into the DNA carrier vehicle.

The present invention also includes a gene sequence which is a chimeric synthetic cDNA encoding GHRH comprising a mouse specific fragment and a species specific fragment and wherein the mouse specific fragment contains the first 45 nucleotides and encodes the first 15 amino acids of the mouse GHRH, and said mouse specific fragment is fused in frame with a species-specific fragment containing 87 nucleotides which encode the 16th to 44th amino acids of a species-specific GHRH. This chimeric sequence provides resistance against dipeptidases.

As used herein, a "chimera" refers to a molecule with genetic material from genetically different organisms.

Furthermore, the present invention can include a species-specific fragment for GHRH encoding a polypeptide from one of the following animal species; porcine, bovine, equine, canine, feline, caprine, avian (chicken, turkey, duck), ovine or fish or encoding for one of the following GHRH polypeptides; SEQ ID NO.5, SEQ ID NO.6, SEQ ID NO.7, SEQ ID NO.8, SEQ ID NO.9, or SEQ 2 Ed ID NO.11.

The present invention also concerns a method whereby skeletal muscle can be transfected in vivo by direct plasmid DNA injection or direct injection of other DNA carrier vehicles.

The present invention further concerns growth promoting myogenic expression plasmid vectors, pSK-GHRH, that drive high-level GHRH expression from animal muscle.

For example, species-specific GHRH can be secreted in vitro, in primary chicken and pig myotube cultures, and in vivo, after the intramuscular injection into regenerating quadriceps muscle of immunocompetent adult C57/B16 mice, or in vivo in the appropriate vertebrate species. Intramuscular injection of pSK-GHRH results in increased serum mGH, several fold over control values, for at least two weeks, and increased liver IGF-1 mRNA levels and enhances animal growth as compared to control animals.

The invention features a plasmid DNA based system which contains a vertebrate gene promoter that provides constitutive transcriptional activity. Other suitable vectors may also be used. The invention may also utilize muscle or other tissue specific promoters, or viral promoters active in animal cells. Human GHRH sequence is not desirable for use in other vertebrate species because it is antigenic and produces antibodies following injection into lower vertebrate animals. The DNA of the invention contains no intervening sequences anywhere in the plasmid DNA. The invention will use the target tissue's transcription, translation and secretory activities to transcribe the GHRH mRNA, correctly translate and then process the GHRH precursor protein, which, in turn, allows for secretion into the systemic blood supply. The increased levels of secreted GHRH will stimulate secretion of GH from the target animal's anterior pituitary.

Several embodiments of the invention involve GHRH expression for ectopic expression of a truncated GHRH from muscle, liver, heart, lung and vascular tissues by a plasmid DNA vector. This vector may contain eukaryotic promoters including various cell or tissue specific promoters (e.g., muscle, endothelial cell, liver), various viral promoters and enhancers, and various GHRH cDNAs isogenically specific for each animal species including porcine, equine, bovine, canine, feline, caprine, ovine, avian (chicken, turkey, duck) or fish. The vector may also contain a chimeric GHRH cDNA composed of the first 15 amino acids of the mouse GHRH following the processed N-terminal histidine, numbered 1, fused in frame with a specific animal GHRH species fragment covering amino acid 16 up to 44 amino acids, a synthetic stop codon, an SV40 or a growth hormone 3' untranslated region containing polyadenylation sites. Any and all of these embodiments may utilize suitable vectors other than a plasmid DNA.

The plasmid of the invention may be incorporated into adenoviral and adenoviral-associated viruses and injected into muscle or into the blood system. DNA taken up into the cellular nuclei of tissue allows for transcription of a messenger RNA encoding a truncated GHRH polypeptide which is then translated into a precursor GHRH protein. The precursor protein requires metalloprotease or other processing to allow for a biologically active GHRH to be secreted. The precursor protein is trimmed to either a N-terminal tyrosine or a N-terminal histidine depending upon the animal GHRH species. Ectopic secretion from muscle and other tissues including liver, pancreas, kidney and heart of the correctly processed GHRH into the blood system, increases the concentration of GHRH in the blood, which then causes a profound stimulation of growth hormone (GH) secretion from the anterior pituitary of the target animal. Skeletal muscle-secreted GHRH is biologically active, as demonstrated by eliciting robust GH release following a single intramuscular injection of 100µ plasmid CMV-GHRH DNA sufficient to elevate GH levels 3 to 4 fold for up to 2 weeks, to enhance liver IFG-1 gene expression and to increase body weight approximately 10%. Thus, plasmid based-GHRH can-serve as a potent GH secretagogue in animals.

One embodiment of the invention includes a novel plasmid vector which is capable of directing high-level gene expression in a skeletal muscle specific manner. A 228 bp fragment of hGHRH, which encodes for the 31 amino acid signal peptide and the entire mature peptide hGHRH(1-44) OH(Tyr1→Leu44) is cloned into a pBS-derived vector. Gene expression is controlled by a 448 bp fragment (−424/+ 24) of the avian skeletal α-actin gene, which contains several evolutionarily conserved regulatory elements that accurately initiate skeletal α-actin transcripts and drives transcription of a variety of reporter genes specifically in differentiated skeletal muscle cells. The GHRH coding region is followed by the 3' untranslated region of human growth hormone cDNA.

In another embodiment the cytomegalovirus promoter and enhancer is used. In a preferred embodiment the promoter is linked to a synthetic GHRH cDNA which contains any non-muscle 3' untranslated region cDNA. In one preferred embodiment a bovine growth hormone 3' untranslated region cDNA is used.

In one embodiment of the invention the plasmid DNA is injected into muscle. In yet another preferred embodiment the promoter GHRHcDNA-3'UTR can be incorporated into a virus, such as an adeno-associated virus for viral infection of muscle.

In another embodiment the invention is incorporated in adenoviruses and allowed to infect a variety of tissues that will then express species specific GHRH mRNA in any tissue the adenovirus infects.

In another embodiment the GHRH vectors are made with species specific GHRH that contains a metalloenzyme processing sequence Arginine-Arginine before a Tyrosine or a Histidine. Each GHRH polypeptide secreted can be made isogenic so that it is identical to the actual animals' GHRH.

Another embodiment of the invention employs a gene switch element in the DNA carrier vehicle. switch element in the DNA carrier vehicle.

In another embodiment a chimera synthetic cDNA encoding GHRH is used that contains the first 45 nucleotides to encode the first 15 amino acids of the mouse GHRH fused in frame with the nucleic acid sequence encoding the 16th to the 44th amino acids of the species-specific GHRH cDNA sequence. This chimeric sequence is effective in providing resistance against proteolytic degradation by dipeptidases.

In other embodiments of the invention the animal species of GHRH encoded for may include: porcine, bovine, equine, canine, feline, caprine, avian (chicken, turkey, duck), ovine and fish.

Other embodiments of the invention utilize nucleotides sequences coding for one of the GHRH polypeptides expressed by any one of SEQ ID NO.5, SEQ ID NO.6, SEQ ID NO.7, SEQ ID NO.8, SEQ ID NO.9, and SEQ ID NO.11. A skilled artisan will readily recognize that these polypeptides can be encoded for by a number of nucleotide sequences.

Other features and advantages of the invention will be apparent from the following detailed description of the invention in conjunction with the accompanying drawings and from the claims.

BRIEF DESCRIPTION OF THE DRAWINGS

FIG. 4 is a chart showing the codon usage frequencies for highly expressed human genes.

FIG. 5 shows the sequences of wild-type GHRH (SEQ ID NO. 1) and a synthetic sequence having optimal codon usage and encoding GHRH (SEQ ID NO. 2).

FIG. 6 shows the nucleotide sequence of a NotI/SalI fragment of the pSK-GHRH plasmid which surrounds the GHRH CDNA insert. The portion coding for GHRH is in bold.

Figure 1:
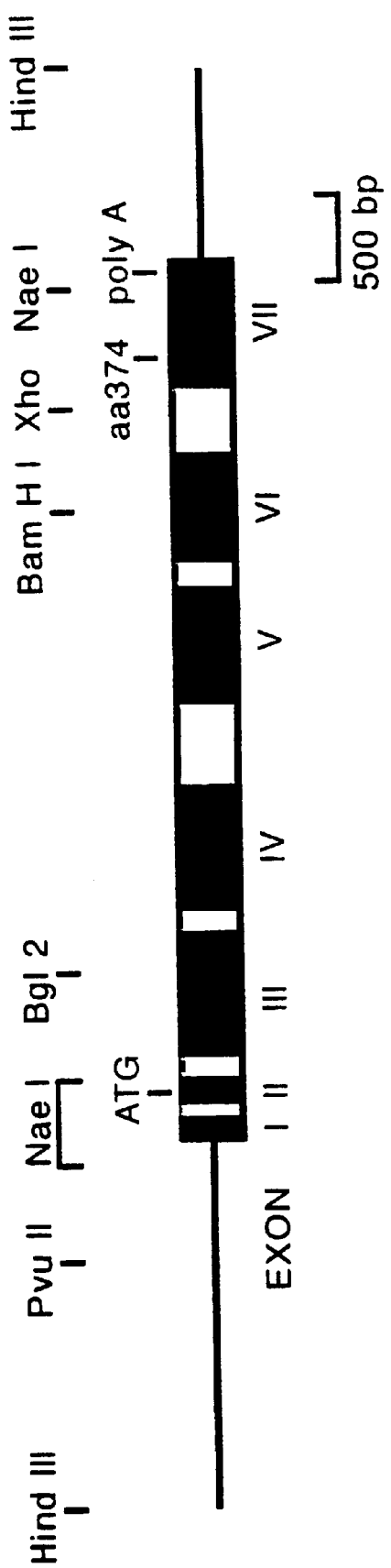
FIG. 1 is a schematic drawing of the chicken skeletal α-actin gene which includes the location of certain unique restriction sites.

The drawings are not necessarily to scale, and certain features of the invention may be exaggerated in scale and shown in schematic form in the interest of clarity and conciseness.

DESCRIPTION OF THE PREFERRED EMBODIMENTS

GHRH administration represents a more physiological alternative of increasing subnormal GH and IGF-I levels (Corpas et al., 1993, *J. Clin. Endocrin. & Metab.* 76:134–138). Even though in mammalian species GH secretion is pulsatile as a result of a complex neuroendocrine regulation process, (Betherat et al., 1995, *Eur. J. Endocrin.* 132:12–24) numerous studies have shown that continuous infusion of GHRH augments GH secretion in normal adults and GH deficient children without evidence of desensitization of the somatotrophs and promotes growth in short, slowly growing children (Low, 1993, *J. Pediatric Endocrin.* 6:15–20). Current limitations of recombinant GHRH therapy are the high cost of recombinant proteins, the short half-life of the peptides in vivo and the requirement for frequent administration (1–3 times/day) given as subcutaneous or intravenous injections.

The human GHRH genetic locus, as well as the gene and cDNA have been characterized (Mayo et al., 1985, *Proc. Natl. Acad. Sci. USA* 82:63–87; Mayo et al., 1983, *Nature* 306:86–88. The gene includes 5 exons and spans 10 kb on human chromosome 20 (Riddell et al., 1985, *Genetics* 11:189–195). Biological activity requires post-translational processing of the GHRH precursor protein. The preprohormones are proteolytically clipped to two mature protein species: (1-40)GHRH with a carboxy terminal group and (1-44)GHRH with a carboxy terminal amide group. Part of exon 2, all of exon 3 and part of exon 4 encode for the 31 amino acids signal peptide and the entire mature peptide (Tyr1→Leu44).

Somatic gene therapy can provide an alternative treatment for growth disorders, catabolic conditions and for the general reduction of GH in the elderly. It is well established that ectopically secreted GHRH, as mature peptide or truncated molecules (as seen with pancreatic islet cell tumors and various located carcinoids) are often biologically active and can even produce acromegaly (Esch et al., 1982), *Biochem. & Biophys. Res. Comm.* 109:152–158; Thorner et al., 1984, *J. Clin. Endocrin. & Metab.* 59:846–849. In a gene therapy approach, the human GHRH CDNA can be targeted into peripheral organs, expressed by the transfected cells and the peptide processed, secreted, transported to the anterior pituitary, where it can stimulate GH release.

Skeletal muscle can be transfected in vivo by direct plasmid DNA injection and an encoded gene can be expressed at significant levels for periods of time, up to about 19 months (Wolff et al., 1992, *Human Mol. Genet.* 1:363–369; Wolff et al, 1990, *Science* 247:1465–1468; Davis et al, 1993, *Human Gene Therapy* 4:151–159; Walls, 1993, *FEBS Lett.* 332:170–182). A limitation of this approach is the relatively low efficiency of gene transfer into nonregenerating adult muscle, though the transfer efficiency can be enhanced by treating the target muscle 3–7 days prior to plasmid DNA injection with 0.75% bupivacaine.

The vectors and methods of this invention provide for the delivery and expression of GHRH in mammalian cells, e.g., in human cells. It has been shown that IGF-I plays an important role in normal muscle development, muscle growth and hypertrophy, muscle regeneration and maintenance/regeneration of peripheral nerves. GHRH increases the levels of GH and IGF-I. Thus, delivery and expression of GHRH from an expression vector is expected to modulate these process.

The following are specific examples of preferred embodiments of the present invention and are not intended to limit the invention. These examples demonstrate how the expression vector systems of the present invention can be used in construction of various cellular or animal models, and how genes can be regulated by sequences within such vectors. The description and utility of such vectors and related vectors is discussed herein and is amplified upon in Schwartz et al., U.S. Pat. No. 5,298,422, entitled "Myogenic Vector Systems,", and co-pending application Schwartz et al., application Ser. No. 08/472,809, entitled "Expression Vector Systems and Method of Use", which are hereby specifically incorporated by reference herein, including drawings. Such vectors can incorporate nucleic acid sequences encoding GHRH and can be used for delivery and expression of GHRH.

Below are provided examples of specific regions of 5'UTR and 3'UTR and/or 3'NCR regions of myogenic genes that can be used to provide certain functionalities to an expression vector, and thus within a transformed cell or animal containing such a vector. Those in the art will recognize that specific portions of these regions can be identified as that containing the functional nucleic acid sequence providing the desirable property, and such regions can be readily defined using routine deletion or mutagenic techniques or their equivalent. Such regions include the promoter, enhancer and cis- and trans-acting elements of a regulatable system. As noted herein, such controlling segments of nucleic acid may be inserted at any location on the vector, although there may be preferable sites as described herein.

Isolation of Chicken Skeletal α-Actin Gene

The nucleic acid sequence of the skeletal α-actin gene has been characterized in chicken, rat, mouse and human. Fornwald et al, 1982, *Nucl. Acids Res.* 10:3861–3876; R. Zakut, 1982, *Nature* 298:857–859; French et al, 1990, *Gene(Amst.)* 88:173–180; Hu et al, 1986, *Mol. Cell. Biol.* 6:15–25; Minty et al, 1986, *Mol. Cell. Biol.* 6:2137–2148. The skeletal α-actin gene is a member of the actin multigene family, .which, in vertebrates, is made up of three distinct classes of actin isoforms termed as "cytoplasmic", "smooth muscle", and "striated" on the basis of their cellular distribution and pattern of expression in adult tissues. The striated actins, α-cardiac and α-skeletal, are co-expressed specifically in cardiac myocytes and skeletal myofibers. Expression of the α-cardiac and α-skeletal actin genes is sequentially up-regulated in developing cardiac and skeletal muscle with the skeletal isoform predominating in adult skeletal muscle. (Vandekerckhove & Weber, 1984, *J. Mol. Biol.* 179:391–413; McHugh et al., 1991, *Dev. Biol.* 148:442–458; Hayward & Schwartz, 1986, *J. Cell Biol.* 102:1485–1493.) The chicken skeletal α-actin gene is the most highly expressed gene in adult chicken skeletal muscle comprising approximately 8% of the poly(A) RNA.

Numerous experiments in vitro and in vivo have established that the regulatory sequences which confer cell type restricted and developmentally regulated expression to the skeletal α-actin gene are primarily concentrated in the immediate 5' promoter region. (Bergsma et al., 1986, *Mol. Cell. Biol.* 6:2462–2475; Taylor et al., 1988, *Genomics*. 3(4): 323–36; Petropoulos et al., 1989, *Mol. Cell. Biol.* 9:3785–3792; Carson et al., 1995, *Am. J. Physiol.* 268:C918–24.)

These regulatory sequences are highly conserved in the promoter regions of all of the known vertebrate skeletal α-actin genes from aves to man. Regulatory sequences derived from the chicken skeletal α-actin gene were utilized in construction of the GHRH expression cassette, though other embodiments can utilize other actin or α-skeletal actin genes.

The primary sequences of the skeletal u-actin genes of the various species were deduced from overlapping cDNA clones. To obtain full genes, the cDNA clones were used to screen genomic DNA. For example, the 25 Kb EcoRI fragment of chicken genomic DNA isolated from a lambda Charon 4A vector, contains the 6.2 Kb skeletal α-actin gene on a single HindIII site of pBR322 is shown in FIG. 1. Chang et al., *Mol. Cell. Biol.* 4:2498–2508 (1984). Nuclear transcription runoffs were used to map the transcriptional domain of the skeletal α-actin gene. The chicken skeletal α-actin control sequences have also been characterized (Bergsma et al., 1986, *Mol. Cell. Biol.* 6:2462–2475). DNA probes which encompassed portions of the 5' noncoding, promoter coding, and the contiguous 3' noncoding regions were cloned into M13 vectors which provided sense and antisense probes. Nuclei isolated from fibroblasts, myoblasts and day 19 embryonic muscle cells were used in in vitro transcription assays to extend RNA transcripts with radioactive tagged nucleotides. Labeled RNA hybridized to dotted DNA probes showed that transcription terminates approximately 1 kb downstream of the skeletal α-actin gene's poly A addition site. This is within a 800 bp PvuII fragment between +2800 and +3600 nucleotides from the start of transcription.

Figure 2:
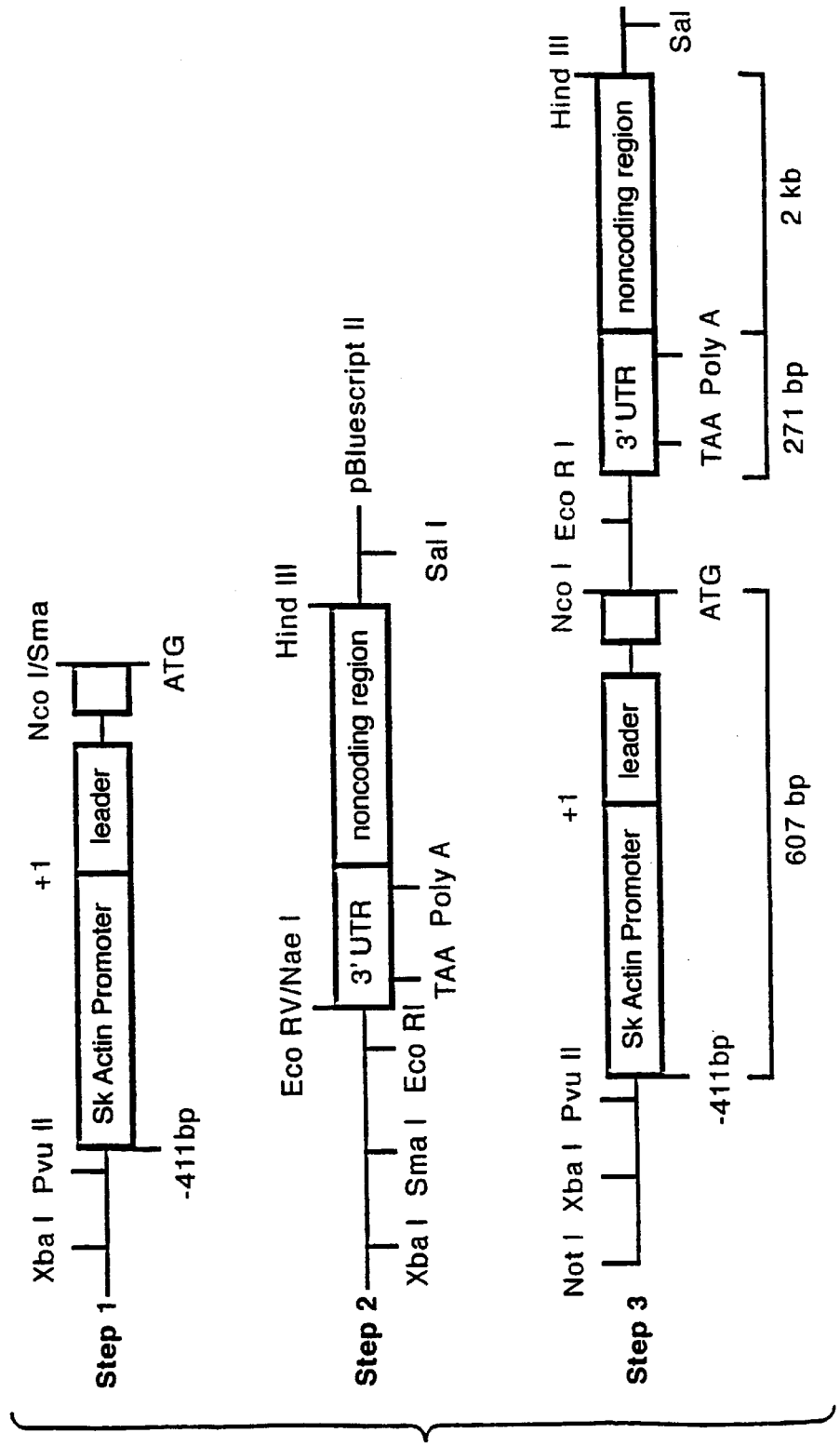
FIG. 2 is a schematic representation of a myogenic vector system.

The 3'UTR and/or 3'NCR can be isolated by restriction endonuclease digestion of the 6.2 Kb actin gene with blunt cutter NaeI, which cuts 30 bp upstream of the translation termination codon TAA. HindIII releases-the 3' most portion of the actin gene from the vector pBR322 (FIG. 2). The 3'UTR and 3'NCR were used to prepare DNA constructs. The skeletal α-actin promoter and DNA flanking sequences (at least 411 nucleotides from the mRNA cap site) and DNA sequences extending through the skeletal 5' noncoding leader, first intron and up to the initiation of translation ATG, converted to a NcoI cloning site at +196, was liberated from a M13 double stranded DNA by XbaI and NcoI digestion, Klenow filled in and then linked into the XbaI and blunt SmaI sites of pBluescript II KS. The NcoI site is regenerated by this cloning step.

For certain vectors described in Schwartz et al., application Ser. No. 08/472,809, the 3'UTR and 3'NCR on the 2.3 kb NaeI/HindIII fragment were directionally cloned into a blunt EcoRV site and the adjacent HindIII site of the pBluescript II KS vector cassette. The EcoRV and NaeI sites are destroyed. The restored NcoI site was used to insert cDNA sequences encoding polypeptides. Another cloning vector was constructed by inserting the skeletal α-actin promoter from −411 to −11 adjacent to the 3'UTR and 3'NCR. This expression vector eliminates the first intron and the skeletal actin 5' leader sequence. These two vectors were used in preparing DNA constructs to test the efficacy of the 3'UTR and 3'NCR.

Results obtained using vectors having a skeletal α-actin/GHRH/GH expression cassette are described below, illustrating the intracellular expression of GHRH from vector constructs and certain results of such expression.

Expression Vector Construction Containing Human GHRH Gene

Constructions containing the skeletal α-actin promoter were linked to the human GHRH cDNA (SEQ ID NO. 1) by standard recombinant DNA techniques as known in the art. Examples of a generalized expression vector structure utilizing skeletal α-actin 5' and 3' sequences is shown in FIG. 2.

The GHRH construction can be made so that a poly A addition site, e.g., the poly A site of GHRH, was linked to the 3'UTR of the GH gene. The sequence was added to increase the stability of nuclear GHRH RNA transcripts.

The poly A skeletal α-actin 3'UTR can also be used in the construction. In this way GHRH RNA transcripts containing the skeletal α-actin 3'UTR are stabilized and accumulate in skeletal muscle cells. In addition, by providing contiguous 3'NCR, GHRH is buffered against outside genomic sequences and is thus more protected from position effects, when integrated into the genome. In addition, by providing natural terminating sequences, the additional regulatory sequences that mark the transcriptional domain of skeletal α-actin prevent read through transcription, improve tissue specificity, developmental timing and transcriptional activity. Presence of 3'NCR sequence allows for a single copy of the integrated vector to produce 40–100% of the transcriptional activity of the endogenous sequences.

Figure 3:
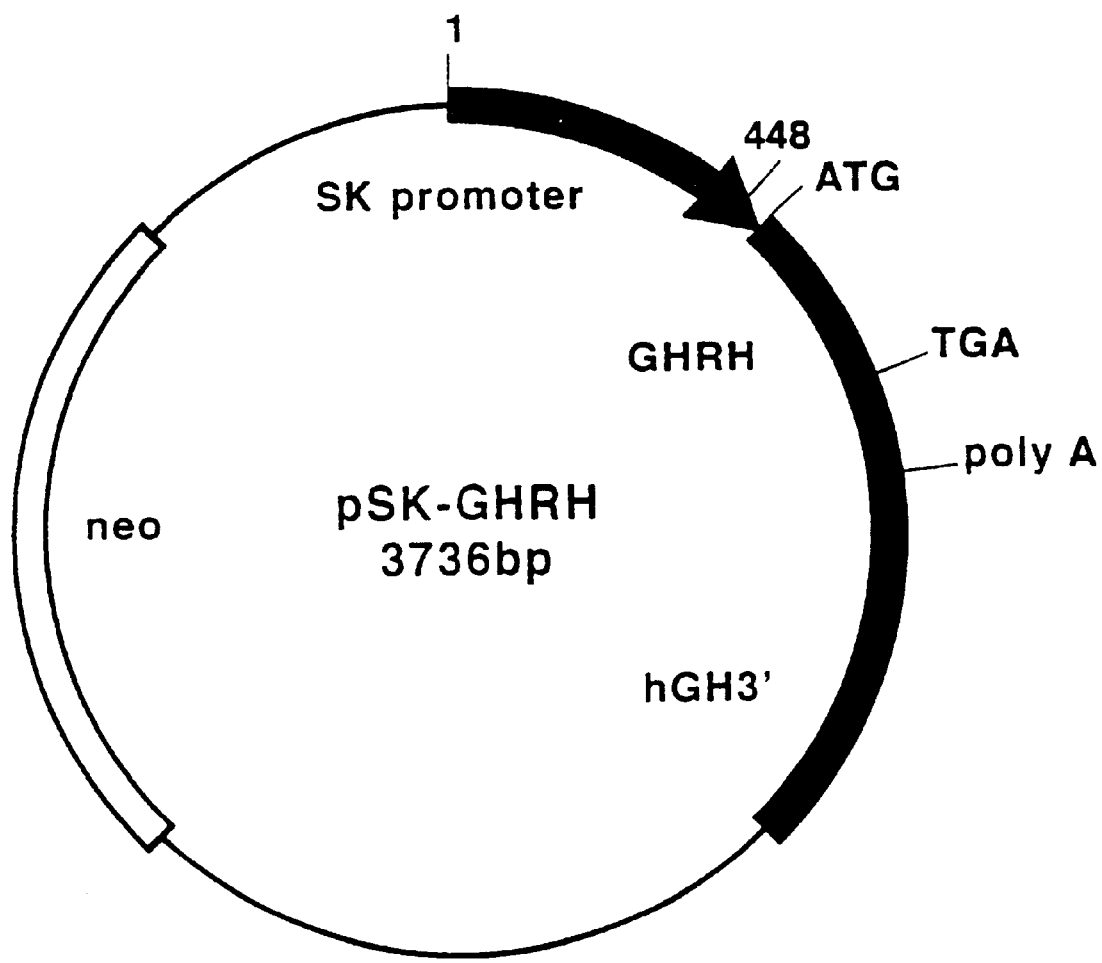
FIG. 3 is a schematic representation of the exemplary plasmid pSK-GHRH.

The exemplary plasmid vector, pSK-GHRH was constructed using pIG0100A and additional constructs (pOGH and pVC0289A). A schematic representation of pSK-GHRH is shown in FIG. 3. The pSK-GHRH expression plasmid contains a hGHRH gene expression cassette in a plasmid backbone containing a kanamycin-resistance (KanR) gene. The plasmid backbone is as described for pIG0552 in co-pending United States provisional application 60/031, 539, Coleman et al., entitled IGF-1 EXPRESSION SYSTEM AND METHODS OF USE, filed Dec. 2, 1996. The hGHRH gene expression cassette of pSK-GHRH contains: 1) a promoter derived from the chicken skeletal α-actin promoter and first intron, 2) the human Growth Hormone Releasing Hormone (hGHRH) cDNA, and 3) a 3'UTR/poly (A) signal from the human Growth Hormone (hGH) 3' untranslated region (3'UTR). The plasmid backbone is derived from pBluescript KS+ (Stratagene) with 1) the substitution of a kanamycin-resistance gene (neo) and prokaryotic promoter (pNEO, Pharmacia) in place of the ampicillin-resistance gene (bla) and 2) the deletion of the fl origin of replication.

The actual construction of pSK-GHRH primarily involved three starting plasmids, pIG0100A, pOGH and pVC0289A.

The chicken skeletal α-actin promoter and first intron were obtained from plasmid pIG0100A (R. Schwartz, Baylor College of Medicine). The hGH 3'UTR was obtained from plasmid pOGH (Nicholas Institute, CA, USA). The hGHRH cDNA 228 bp fragment (part of exon 2, all exon 3 and part of exon coding for the 31 amino acid signal peptide and entire mature hGHRH1-44 peptide Tyr1→Leu44) was utilized. pIG0100A contains the chicken skeletal αactin promoter and first intron, human hIGF-1 cDNA, and chicken skeletal α-actin 3' untranslated region and 3' flanking sequence in pBluescript KS+. As indicated above, the plasmid backbone, pVC0289A, includes the kanamycin-resistance gene, pUC origin of replication, and a multicloning site.

The construction scheme used to produce pSK-GHRH from pIG0100A, pOGH, and pVC0289A incorporated the following steps. In order to construct hybrid pSK-GHRH, a 448 bp fragment (−424/+24) of avian skeletal α-actin promoter (SK) was used (Lee et al., 1994, *J. Oncogene* 9:1047–1052; Chow et al., 1991, *PNAS* 88:1301–1305). The hGHRH cDNA 228 bp fragment (part of exon 2, all exon 3 and part of exon 4) coding for the 31 aminoacid signal peptide and entire mature hGHRH1-44 peptide (Tyr1-Leu44) has been cloned into BamHl/HindIII sites of pVC0289. The 3' untranslated region of hGH cDNA Smal blunted/EcoRl 622 bp fragment was cut from the commercial pOGH plasmid (Nichols Institute, CA, USA) and cloned into Clal blunted/EcoRl sites of pVCO 289. The sequence of a NotI/SalI fragment of the plasmid, which includes the SK promoter, GHRH cDNA, and hGH 3' region is shown in FIG. 6.

The GHRH cDNA and plasmid sequences described herein are believed to be correct, however, the possible presence of a small percentage of nucleotide sequence errors will not impair the use of this invention. Those skilled in the art will understand how to obtain sequences coding for GHRH, e.g., hRHRH, such as by isolating a GHRH cDNA from a cDNA library using a probe or probes derived from the published GHRH sequence or from the sequence described herein. Such a sequence can be sequenced by routine methods to confirm or obtain the correct GHRH coding sequence. The 5'UTR and 3'UTR sequences reported herein can likewise be obtained by routine methods. Based on the present disclosure, those skilled in the art will also understand how to construct a vector containing a sequence encoding GHRH, which can be used for delivery and expression of the GHRH in vivo.

Also, in addition to sequences encoding natural GHRH, e.g., the sequence encoding GHRH (1-44), other sequences encoding functional GHRH derivatives can be used, such as a sequence encoding hGHRH (1-40), or modified sequences which encode a GHRH derivative differing in one or a few amino acids but which retains the GH and IGF-1 related functions of native GHRH. Preferably, the encoded GHRH derivative will differ from a native GHRH, e.g., hGHRH (1-44) or hGHRH (1-40), by the addition, deletion, substitution, or a combination of these changes at a small number or amino acid residues. A small number is preferably 5 or fewer, more 3 or fewer, still more preferably 2 or fewer, and most preferably is one amino acid.

In addition to sequences encoding native length al GHRH or a functional derivative, a coding sequence can also be used which encodes a preprohormone which can be proteolytically cleaved to produce an active GHRH molecule or derivative. Such sequences are exemplified by natural hGHRH coding sequences which encode a polypeptide sequence which is cleaved to produce both hGHRH (1-44) and hRHRH (1-40) mature polypeptides.

In the pSK-LacZ construct, the β-galactosidase gene of *Escherichia coli*, with a nuclear localization signal (nls), is driven by the same SK promoter, but contains the 3'UTR of skeletal α-actin gene (French et al., 1990, *Gene* 88:173–180).

Instead of the natural sequence coding for GHRH, it is advantageous to utilize synthetic sequences which encode GHRH. Such synthetic sequences have alternate codon usage from the natural sequence, and thus have dramatically different nucleotide sequences from the natural sequence. In particular, synthetic sequences can be used which have codon usage at least partially optimized for expression in a human. The natural sequences do not have such optimal codon usage. Preferably, substantially all the codons are optimized.

Optimal codon usage in humans is indicated by codon usage frequencies for highly expressed human genes, as shown in FIG. 4. The codon usage chart is from the program "Human_High.cod" from the Wisconsin Sequence Analysis Package, Version 8.1, Genetics Computer Group, Madison, Wis. The codons which are most frequently used in highly expressed human genes are presumptively the optimal codons for expression in human host cells, and thus form the basis for constructing a synthetic coding sequence.

However, rather than a sequence having fully optimized codon usage, it may be desirable to utilize an GHRH encoding sequence which has optimized codon usage except in areas where the same amino acid is too close together or abundant to make uniform codon usage optimal.

In addition, other synthetic or derivative sequences can be used which have substantial portions of the codon usage optimized, for example, with at least 50%, 70%, 80% or 90% optimized codons. Other particular synthetic sequences for GHRH can be selected by reference to the codon usage chart in FIG. 4. A sequence is selected by choosing a codon for each of the amino acids of the polypeptide sequences. DNA molecules corresponding to each of the polypeptides can then by constructed by routine chemical synthesis methods. For example, shorter oligonucleotides can be synthesized, and then ligated in the appropriate relationships to construct the full-length coding sequences.

A particular preferred synthetic GHRH coding sequence is provided in SEQ ID No. 2.

Myogenic Cell Cultures and DNA Transfer

Minimal Essential Medium (MEM), horse serum, gentamycin, Hank's Balanced Salt Solution (HBSS), lipofectamine were obtained from Gibco BRL, NY, USA.

Primary chicken myoblast culture was obtained as described (Bergame et al., *J. Molec. & Cell. Biol.* 6:2462–2475). The cells were plated 24 h prior to transfection at a density of 1.5 million cells/100 mm plate, in MEM supplemented with 10% horse serum (HIHS) 5% chicken extract (CE) and gentamycin. Cells were maintained in a humidified 5% $CO_2$ 95% air atmosphere at 37□C.

Cells were transfected with 4 μg of pSK-GHRH or pSK-LacZ per plate using lipofectamine, according to the manufacturer instructions. After transfection, the cells were changed in MEM, 2% HIHS, 2% CE for at least 24 h to allow differentiation.

Primary pig myoblasts culture was obtained as described (Doumit & Merkel, 1992, *Tissue & Cell* 24:253–262). The cells were plated at a density of 1 million cells/100 mm plate and maintained in growth media for 2–3 days. The cells were passed for 2 times prior to transfection. The transfection and differentiation was made in the same conditions as for the primary chicken myoblast culture. The media and cells were harvested for analysis 48, 72 and 96 h postdifferentiation in both cases. The efficiency of transfection estimated by β-galactosidase histochemistry on control plates was 10%.

One day before harvesting, cells were washed twice in HBSS and changed in MEM, 0.1% BSA. The collected media was conditioned by adding ¼ volumes of 1% triflouroacetic acid (TFA) and 0.001% phenylmethylsulfonylflouride (PMSF), frozen at −80° C., lyophilized, purified on C-18 Sep-Columns (Peninsula Laboratories, CA, USA), relyophilized and used in RIA or resuspended in media conditioned for primary pig anterior pituitary culture. The pig anterior pituitary culture was obtained by Dr. Thomas H. Welsh Jr. in the Department of Animal Sciences at Texas A&M University as described (Tanner et al., 1990, *J. Endocrinol.* 125:109–115). Pig GH was assayed as described (Barb et al., 1991, *Domestic Animal Endocrinology* 8:117–127). The samples and controls were assayed as described in quadruplicate. The cells were homogenized directly into Ultraspec RNA reagent (Biotecx Laboratories, TX, USA) for the isolation of total RNA.

Measurement of Secreted Levels of GHRH from GHRH Gene Delivery by the Expression Vector A. In vitro expression of pSK-GHRH. We characterized a novel plasmid vector able to express in a skeletal muscle specific manner a high level of a target protein, hGHRH. A 228 bp fragment of hGHRH (part of exon 2, all exon 3 and part of exon 4), which encode for the 31 aminoacid signal peptide and the entire mature peptide hGHRH(1-44)OH (Tyr1→Leu44) (Mayo et al., 1985, *PNAS* 82:63–67) was cloned into a pBS-derived vector. The coding sequence was controlled by a 448 bp fragment (−424/+24) of the avian skeletal α-actin gene, which contain several evolutionarily conserved regulatory elements that accurately initiate skeletal α-actin transcripts and drive transcription of a variety of reporter genes specifically in differentiated skeletal muscle cells (Bergame et al, 1986, *J. Mol. & Cell. Biol.* 6:2462–2475; Chow et al., 1990, *J. Mol. & Cell. Biol.* 10:528–538; Lee et al., 1994, *J. Oncogene* 9:1047–1052). The coding region was followed by the 3' untranslated region of human growth hormone cDNA.

In vitro expression of pSK-GHRH was first examined in transiently transfected chicken primary myoblasts. The pSK-GHRH transfected cells and the controls, transfected with pSK-LacZ were placed into differentiation media for 24–72 h to initiate withdrawal from the cell cycle and induce post-fusion differentiation, then changed into a minimal serum-free media for a 24 h pulse. Cells were harvested 48 to 96 h post-differentiation. Northern blot analysis of cellular extracted RNA treated with DNase, showed the expected size transcripts of 0.35 kb, in myoblasts transfected with pSK-GHRH, but not in pSK-LacZ transfected myoblasts. The expression of pSK-GHRH peaked at 48 h postdifferentiation and was reduced thereafter in comparison to the glycolytic enzyme GAPDH. This pattern of activation is characteristic of the promoter utilized, which induces high levels of transgene expression in myotubes but not in replicating myoblasts (Bergame et al, 1986, *J. Mol. & Cell. Biol.* 6:2462–2475; Chow et al., 1990, *J. Mol. & Cell. Biol.* 10:528–538; Lee et al., 1994, *J. Oncogene* 9:1047–1052).

Figure 7:
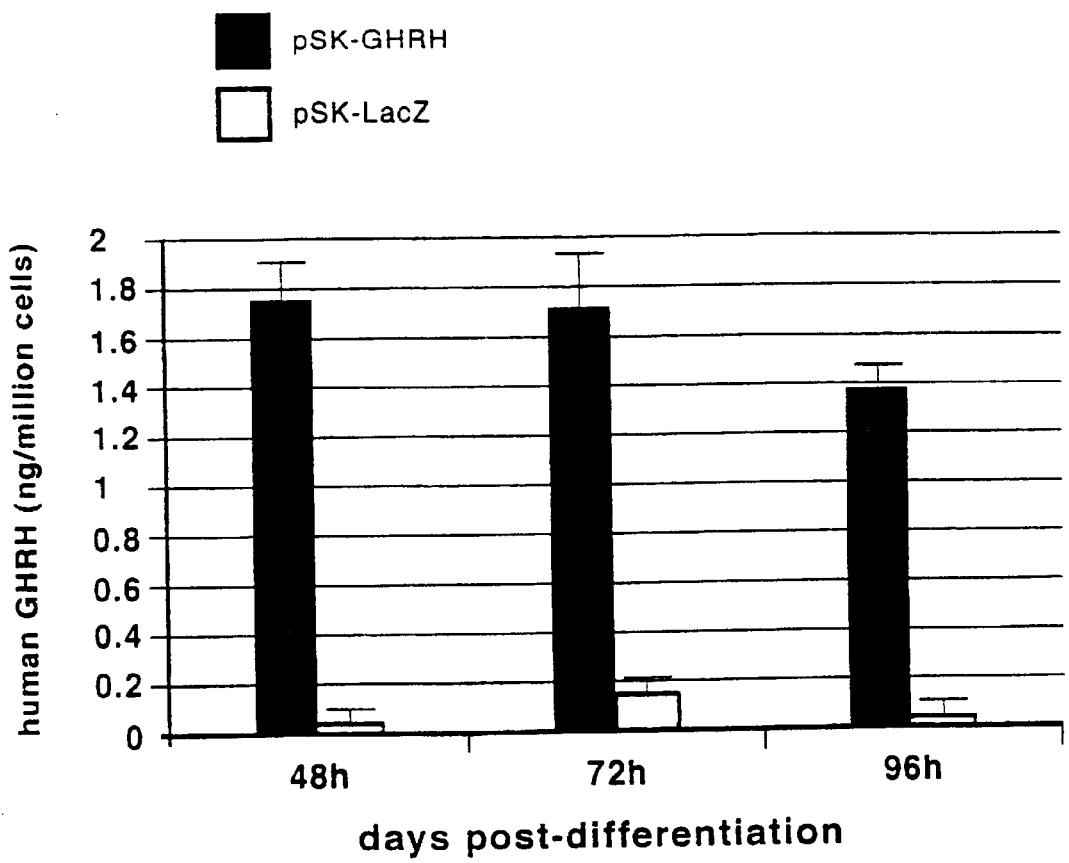
FIG. 7 shows the level of human GHRH secreted in the culture media of transfected chicken primary myoblasts as measured by specific RIA: pSK-GHRH (black, n=8), compared with pSK-LacZ (white, n=8). The results are presented as means±s.e.m (*, p value is ≦0.002).

Conditioned media from pSK-GHRH and pSK-LacZ transfected myoblasts were harvested and purified on C18 Sep-Columns (which served two purposes: to separate the peptide to be assayed from potentially interfering substances and to concentrate the samples) to determine levels of radioimmunoassayable hGHRH. Chicken primary myoblasts transfected with pSK-GHRH produced approximately 1.7 ng hGHRH(1-44)OH/million cells/h. Media from pSK-LacZ control transfected cells did not contain hGHRH higher than the untransfected controls (FIG. 7). The decrease in hGHRH secreted into the media at 96 h correlated with the decrease of mRNA between the 72 and 96 h time-points. We concluded that the skeletal fibers transfected with pSK-GHRH are expressing and secreting at a high level hGHRH (1-44)OH.

Figure 8:
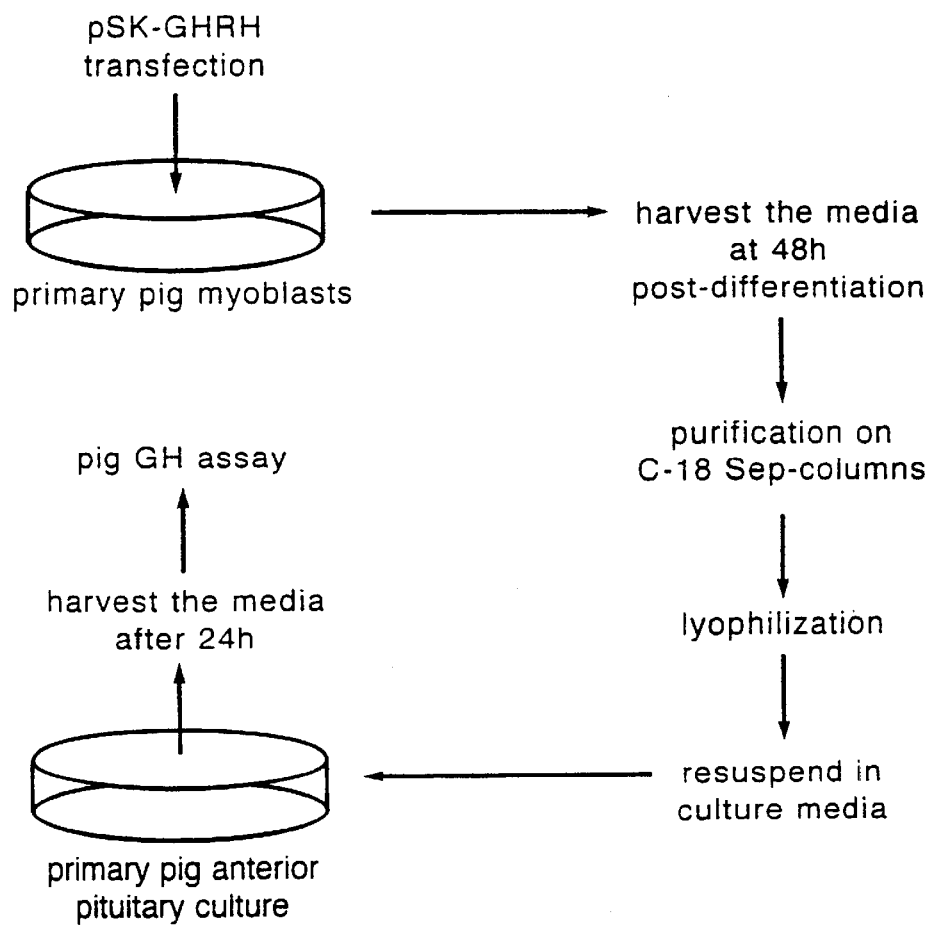
FIG. 8 is the experimental design for stimulation of the GH secretion by hGHRH secreted by primary pig myoblasts (ppm) transfected with PSK-GHRH.
Figure 9:
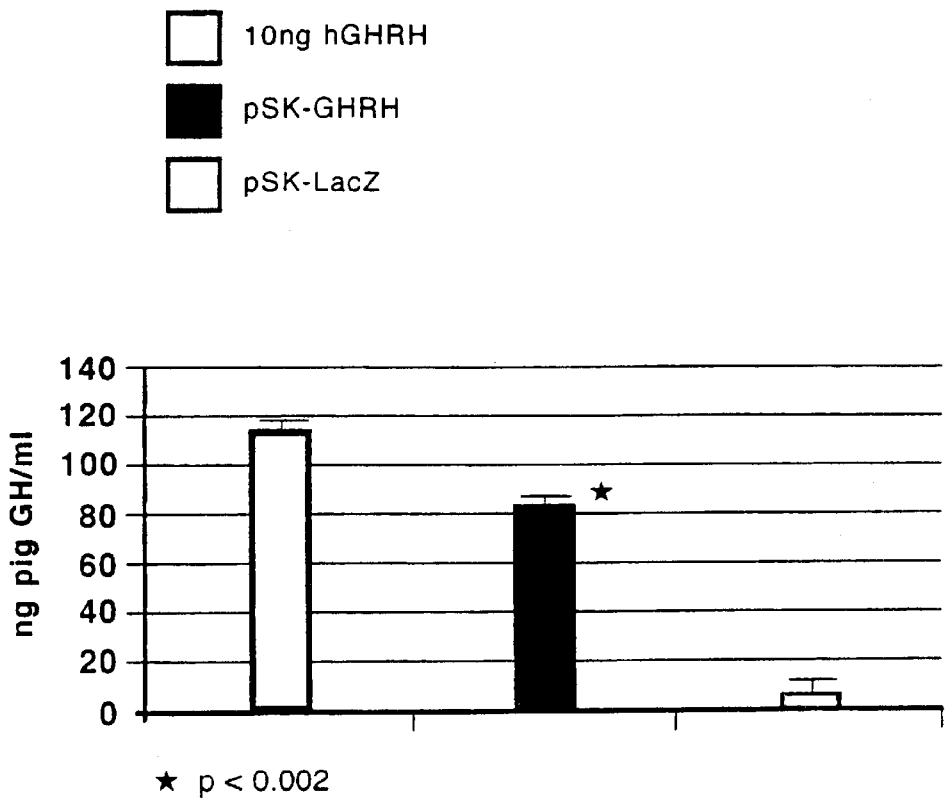
FIG. 9 shows pig GH release in primary pig anterior pituitary culture after 24 h challenge in response to: 10 ng hGHRH (white, n=4)=long of synthetic hGHRH(1-44)NH$_2$ have been mixed in the ppm culture media; pSK-GHRH (black, n=4)=the conditioned culture media from 1 million ppm transiently transfected with pSK-GHRH; pSK-LacZ (gray, n=4)=the conditioned culture media from 1 million ppm transiently transfected with pSK-LacZ. The results are presented as means±s.e.m.(*, p value for PSK-GHRH ≦0.002).

B. In vitro activity of pSK-GHRH. Since anterior pituitary is the natural target of GHRH stimulation, we determined the biological activity of secreted GHRH from the media of pSK-GHRH transfected primary pig myoblasts (FIG. 8). The in vitro potency of the hGHRH (1-44)OH molecule secreted by primary pig myoblasts (ppm) transiently transfected with pSK-GHRH was compared to that of the hGHRH (1-44)NH$_2$ synthetic molecule for the ability to stimulate GH release in primary pig anterior pituitary cells after a 24 h stimulation at 37□ C. GH release from the primary pig anterior pituitary cells rose from values of 7±2 ng/ml to 82.5±3.1 ng/ml (p≦0.002) when stimulated with the culture media from 1 million primary pig myoblasts transiently transfected with pSK-GHRH. This value equals 72% of that obtained when the pituitary cells were stimulated with myoblast serum-free media mixed initially with 10 ng synthetic hGHRH (1-44)NH$_2$ then purified and processed as the test media (GH release in this case was 115±3.2 ng/ml) (FIG. 9).

Thus, hGHRH(1-44)OH secreted by skeletal pig myocytes transfected with pSK-GHRH retains functional activity in pig pituitary cell culture and induces secretion of physiologically significant levels of GH. This is an important finding, because the pig (1-44)GHRH, as well as the human molecule, is amidated, while the molecule which is expressed by our construct is non-amidated at amino acid 44. It has been shown in previous studies using synthetic molecules that hGHRH(1-44)OH is 30% less effective in releasing GH than the (1-44) amidated form (Ling et al, 1984, *Biochem. & Biophys. Res. Comm.* 123:854–861).

Insertion of Expression Vectors into Transgenic Mice

Transgenic mice carrying GHRH containing vectors can be generated by standard methods, e.g., by standard oocyte injection (Brinster, et al, *Proc. Natl. Acad. Sci. USA* 82:4438–4442 (1958)) and bred to demonstrate stable transmission of transgenes to subsequent generations. Transgenics can be identified by polymerase chain reaction or Southern genomic DNA blotting analysis from tail cut DNA. Transgenics can be tested for muscle specific expression of the transferred GHRH vector by RNA blotting of total RNA isolated from several tissues.

Somatic Gene Transfer to Skeletal Muscle in Vivo

In vivo expression and activity of pSK-GHRH. In addition to the in vitro determinations of GHRH expression from chicken primary myoblasts and the induction of GH secretion from pig primary anterior pituitary cells by GHRH expressed in pig primary myoblasts, we determined whether a single injection of 100 μg pSK-GHRH in adult immunocompetent C57B16 mice would be sufficient to elicit enhanced GH systemic levels.

Five days before the plasmid administration, the mice were injected with 0.75% bupivacaine into the left quadriceps muscle. On day 0, animals were anesthetized and injected into the same muscle either with 100 μpg of pSK-GHRH or pSK-LacZ in 100 μl PBS. Three to 21 days later, the animals were weighted, killed, injected muscle collected and frozen in liquid nitrogen and the blood collected by transcardiac puncture.

Figure 10:
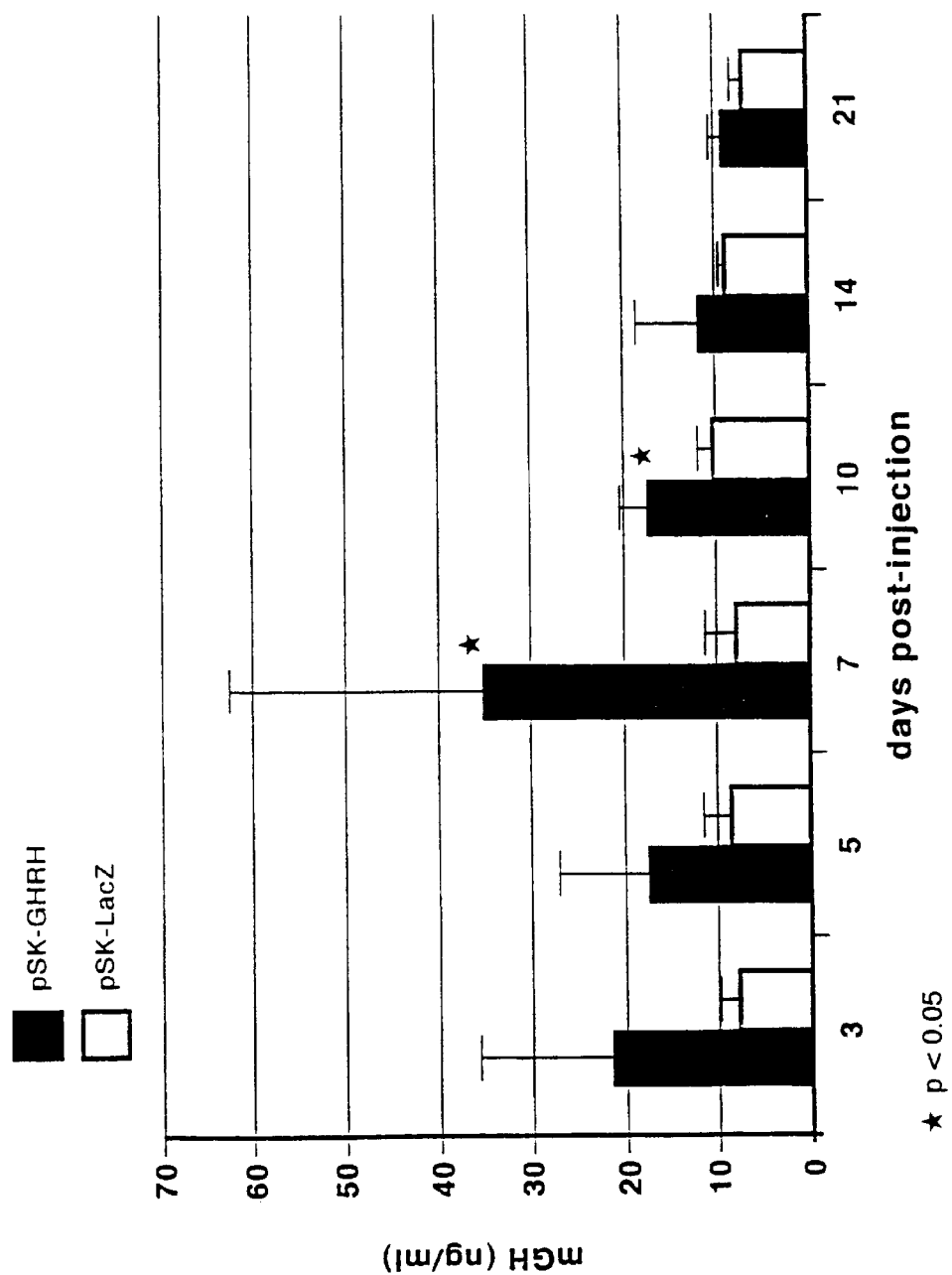
FIG. 10 shows expression of pSK-GHRH assessed by RT-PCR at 3–21 days after i.m. injection of 100 μg pSK-GHRH in the regenerating left quadriceps muscle of adult C57/B16 mice.

The in vivo expression of pSK-GHRH was assessed by RT-PCR on injected muscle (FIG. 10). Muscle RNA was DNase I treated in order to eliminate the injected plasmid, reextracted and 1 μg of total RNA was used in the reverse transcriptase reaction. Only the PSK-GHRH injected muscles showed a 254 bp PCR fragment when using GHRH specific primers. The pSK-LacZ injected muscles showed a 497 bp PCR fragment for mouse cytoskeletic □-actin, used as a control, but not for GHRH. The efficiency of DNase treatment to eliminate plasmid DNA was checked using RNA from pSK-GHRH injected muscle. When the reverse transcriptase was omitted from the reaction, no amplification was seen.

Serum mGH in the pSK-GHRH quadriceps injected animals were significantly elevated compared with mGH levels in serum from control mice. Time course analysis of mGH as a response to pSK-GHRH injections showed stimulation at 3 days post-injection (21.54±15.29 ng/ml vs. 7.53±0.57 ng/ml, n=6), peaked at 7 days post-injection (36.28±27.28 ng/ml vs. 8.2±1.9 ng/mi, $p \leq 0.05$, n=6) and declined gradually to the base-line by 21 days postinjection (9.16±2.54 ng/ml vs. 6.76±0.89 ng/ml, n=6).

Another indication of increased systemic levels of GH would be the linkage with the IGF-I biosynthesis in the liver. Thus, liver IGF-I expression of injected mice and controls was evaluated by Northern blot analysis of total RNA. Elevated mIGF-I mRNA expression was detected in all pSK-GHRH injected animals in comparison to a relatively stable baseline of IGF-I in RNA with those animals injected with pSK-LacZ. We observed increased IGF-I mRNA starting as soon as 3 days post-injection and maintained at least up to 21 days.

Figure 11:
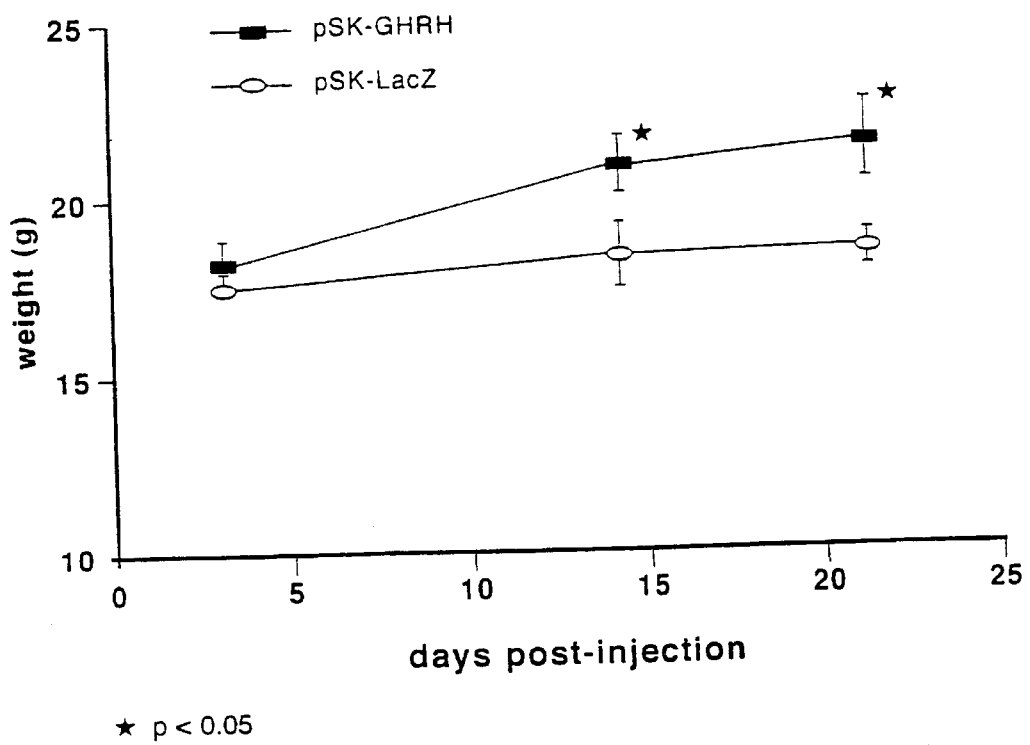
FIG. 11 shows body weight at different time points after a single injection in the regenerating left quadriceps muscle of adult mice of pSK-GHRH (black, n=6), compared to that of age-matched pSK-LacZ injected animals (white, n=6). The results are presented as means±s.e.m. Significant difference *, p≦0.05 and p≦0.03, was observed at day 14 and day 21, respectively.

Finally, hGHRH secreted into the systemic circulation after intramuscular injection of pSK-GHRH A enhanced growth in normal mice (FIG. 11), as shown by significant differences in their total body mass at 14 days (21.11±1.47 g vs. 18.62±0.4 g, $p \leq 0.043$) and 21 days (21.86±1.45 g vs. 18.8±0.42 g, $p \leq 0.028$) after a single injection of pSK-GHRH.

We observed only a transient activity of pSK-GHRH in vivo, after i.m. injection in adult mice, a fact most probably due to the humoral immune response targeted against hGHRH, a heterologous protein in mouse (Yao et al., 1994, Gene Therapy 1:99–107; Tripathy et al., 1996, PNAS 93:10876–10880; Tripathy et al, 1996, Nature Med. 2:545–550).

Our results demonstrate that the i.m. injected pSK-GHRH could be used to produce physiological levels of GHRH in the circulation of adult animals. This data suggests that it is possible to restore endogenous GH secretion to children and adults with GH deficiencies in a more physiological and less expensive way compared with the classical therapies.

Enhanced Vector Expression in Intact Muscle

Intact plasmid DNA in a sterile 20% sucrose solution (wt/vol) can be injected into mature avian or mammalian muscle. Following a single injection the vector DNA is stable for at least 30 days as a non-integrated extrachromosomal circular DNA in muscle nuclei and, is transcriptionally active. Wolf et al., Science, vol. 247, pp. 1465–1468 (1990). However, greater than 99% of the injected DNA is degraded in muscle under the Wolff protocol (Wolff, et al, BioTechniques 11:4374–485 (1991)). This protocol can be improved by increasing the uptake of plasmid DNA into muscle and reducing vector degradation. The procedure of the present invention can use expression vector DNA coated with the relevant transcriptional regulatory factors, the human serum response factor and other human associated nuclear proteins, such as histone, and transcription initiation factors to enhance uptake and stability. The regulatory proteins protect the DNA against muscle nucleases and facilitate the uptake of the protein coated DNA into myogenic nuclei.

The expression vector forms a protein/DNA complex by the sequence specific binding of the serum response factor with the inner core CCXXXXXXGG (where X can be either A or T; SEQ ID NO. 3) of the serum response element and by the addition of histone. The interaction with the inner core of the promoter facilitates myogenic cell type restricted expression of the skeletal α-actin gene. The serum response factor, transcription initiation factor, transregulatory factor and histones are added to the expression vector by an in vitro binding reaction to form a reconstituted protein/DNA complex.

Coating the Expression Vector System

A specific formulation involves coating the vector with elements of the transcription initiation complex and histone. This formulation is used both to enhance delivery of the vector to the cell and to enhance expression of the vector within the cell.

The following protocol was used to bacterially express and purify human serum response factor (SRF). Plasmid pARSRF-Nde is a T7 polymerase vector (Studier, F. W. and Moffatt, J. Mol. Biol. 189:113–130 (1986)) which produced full-length SRF protein upon IPTG (isopropyl-B-D-thiogalactopyranoside) induction. (Manak et al., Genes and Development 4:955–967 (1990)). E. coli BL21 harboring the plasmid was grown at 37° C. to an $OD_{600}$ of 0.4 in TYP medium supplemented with ampicillin (50 μg/ml). Synthesis of SRF was then induced with 1 mM IPTG for 2.0 hr, after which cells were spun down, washed once in TE buffer (10 mM Tris-HCl, 1 mM EDTA, pH 7.0) and resuspended in a 40× packed cell volume and dialyzed against (10 mM HEPES [N-2 hydroxyethylpiperzine-N-2-ethansulfonic acid, pH 7.4], 60 mM KCl, 1 mM 2-mercaptoethanol 0.5 mM EDTA, 0.5 mM phenylmethylsulfonyl fluoride and 10% glycerol). Cells were disrupted on ice by sonication. The lysate was clarified by centrifugation (15,000×g for 20 min.) and the high speed supernatant containing overexpressed SRF was stored at −80° C. Partial purification of SRF was done as follows. A 10 ml amount of the lysate was applied to a 10 ml phosphocellulose column equilibrated with column buffer (same as dialysis buffer as described above) and 0.05% Nonidet P-40. The flow through fractions were collected and applied to a 5-ml heparin agarose column. The column was washed with 0.35 M KCl and SRF was eluted with 0.5 M KCl. SRF was then dialyzed and stored at −80° C.

Approximately, a ratio by weight of 5 to 1 SRF protein to expression vector DNA was allowed to incubate together in a solution containing 10 mM. Tris-HCl (pH 8.0, 0.1 mM EDTA, 2 mM dithiothreitol, 5% glycerol plus 100 mM KCl. The binding of SRF to the actin promoter has been verified by DNA binding assays and by nuclease footprint protection assays as shown in the art. Transcription initiation factors such as the TATA box protein (TBP) and other initiation factors such as TFIIB, E and F are eluted from purified HeLa cell nuclei by the protocol of Dignam et al., *Mol. Cell. Biol.* 10:582–598 (1983) with 0.42M KCl in the above dialysis buffer. Nuclear lysates containing transcription initiation factors are mixed together with the SRF-DNA plasmid at a ratio of 10 parts protein to one part SRF-DNA to help form a preinitiation complex which is dialyzed for 24 hours. Finally, a crude histone preparation which is stripped from HeLa nuclei in 6M urea, 2M NaCl is dialyzed against low salt dialysis buffer. The full complement of histone are slowly added to a final ratio of 1 to 1 (histone to the SRF-protein DNA complex) to form nucleosome particles over nonprotected DNA. The addition of histone will protect regions of DNA to a greater extent than naked DNA from cellular nucleases.

The nucleoprotein complex is then further formulated with a lipid base, nonaqueous base and/or liposomes for direct injection into muscle. Because of the abundance of specific transcription factors, which contain nuclear targeting sequences, expression vector DNA is readily delivered, and taken up into muscle nuclei.

The vector can also be prepared in a formulation with other DNA binding compounds. For example, the vector can be prepared with polyvinyl pyrrolidone (PVP). PVP is a synthetic polymer consisting of linear 1-vinyl-2-pyrrolidone groups. PVP is commercially available with various degrees of polymerization and molecular weights. Pharmaceutical grade PVP is marketed under the trade names Plasdone (International Specialty Products, ISP) and Kollidon (BASF). ISP describes the typical properties of Plasdone C-30 in its product literature. Plasdone C-30 has a weight average molecular weight of 50,000 g/mol.

PVP is found to interact with DNA by hydrogen bonding. PVP is also found to protect DNA in vitro from nuclease (DNase 1) degradation. Reporter genes (CMV-CAT or CMV-β-gal) were formulated in PVP solutions and injected into rat tibialis muscles after surgical exposure. The results showed that DNA formulated at 3 mg/mL in 5% PVP in 150 mM NaCl led to the highest enhancement of gene expression over DNA formulated in saline. The levels of gene expression using lower molecular weight PVP (Plasdone C-15) were approximately 2-fold lower than levels of gene expression using formulations made with Plasdone C-30. When rat tibialis muscles were injected with DNA formulated in either saline or 5% PVP (Plasdone C-30), immunochemical staining for β-galactosidase revealed that the staining was more widely distributed in muscles treated with the formulated DNA. The staining also showed that the PVP formulation resulted in an increase in the number of cells expressing β-gal and that these cells were distributed over a larger area as compared to DNA injected in saline. It is suggested that the increased tissue dispersion of DNA using PVP formulations is due to a hyper-osmotic effect in the muscle. DNA (3 mg/mL) in 5% PVP (Plasdone C-30) in 150 mM NaCl exerts an osmotic pressure of 341±1 mOsm/kg $H_2O$.

An exemplary formulation of the hGHRH plasmid is a three-vial system, with product components to be mixed just prior to use. The product components are:
1. Human GHRH plasmid in sterile water;
2. Lyophilized PVP (polyvinylpyrrolidone; Plasdone C-30, Povidone U.S.P.); chemical formula $(C_6H_9NO)_n$;
3. 115 mM sodium citrate buffer (pH 4) in 5% NaCl.

The expression vector can also be delivered as described below.

Administration

Administration as used herein refers to the route of introduction of a vector or carrier of DNA into the body. Administration can be directly to a target tissue or by targeted delivery to the target tissue after systemic administration. In particular, the present invention can be used for treating disease by administration of the vector to the body in order to establishing controlled expression of any specific nucleic acid sequence within tissues at certain levels that are useful for gene therapy.

The preferred means for administration of vector and use of formulations for delivery are described above. The preferred embodiment is by direct injection using needle injection or hypospray.

The route of administration of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

Muscle cells have the unique ability to take up DNA from the extracellular space after simple injection of DNA particles as a solution, suspension, or colloid into the muscle. Expression of DNA by this method can be sustained for several months.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determines the bioavailability of the vector within the body. Other elements of the formulation function as ligand which interact with specific receptors on the surface or interior of the cell. Other elements of the formulation function to enhance entry into the cell, release from the endosome, and entry into the nucleus.

Delivery can also be through use of DNA transporters. DNA transporters refers to molecules which bind to DNA vectors and are capable of being taken up by epidermal cells. DNA transporters contain a molecular complex capable of noncovalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Ser. No. 07/855,389, entitled "A DNA Transporter System and Method of Use, filed Mar. 20, 1992, now abandoned; (2) Woo et al., PCT/US93/02725, International Publ. WO93/18759, entitled "A DNA Transporter System and method of Use", (designating the U.S. and other countries) filed Mar. 19, 1993; (3) a continuation-in-part application by Woo et al., entitled "Nucleic Acid Transporter Systems and Methods of Use", filed Dec. 14, 1993, U.S. Ser. No. 08/167,641; (4) Szoka et al., U.S. Ser. No. 07/913,669, entitled "Self-Assembling Polynucleotide Delivery System", filed Jul. 14, 1992 and (5) Szoka et al., PCT/US93/03406, International Publ. WO93/19768 entitled "Self-Assembling Polynucleotide Delivery System", (designating the U.S. and other countries) filed Apr. 5, 1993.

Transfer of genes directly into muscle has been very effective. Experiments show that administration by direct injection of DNA into muscle cells results in expression of the gene in the area of injection. Injection of plasmids containing GHRH results in expression of the gene for months at relatively constant levels. The injected DNA appears to persist in an unintegrated extrachromosomal state. This means of transfer is the preferred embodiment.

Another preferred method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. One element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblasts genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs gene therapy and the genetically engineered cells can also be easily put back with out causing damage to the patient's muscle. Similarly, keratinocytes may be used to deliver genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the El region of the virus genome with the vector elements described in this invention including promoter, 5'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

The chosen method of delivery should result in expression of the gene product encoded within the nucleic acid cassette at levels which exert an appropriate biological effect. The rate of expression will depend upon the disease, the pharmacokinetics of the vector and gene product, and the route of administration, but should be between 1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Cell Transfection and Transformation

One aspect of the present invention includes cells transfected with the vectors described above. Once the cells are transfected, the transformed cells will express the protein or RNA encoded for by the nucleic acid cassette. Examples of proteins include, but are not limited to polypeptide, glycoprotein, lipoprotein, phosphoprotein, or nucleoprotein.

The nucleic acid cassette which contains the genetic material of interest is positionally and sequentially oriented within the vectors such that the nucleic acid in the cassette can be transcribed into RNA and, when necessary, be translated into proteins or polypeptides in the transformed cells.

A variety of proteins can be expressed by the sequence in the nucleic acid cassette in the transformed cells. Those proteins which can be expressed may be located in the cytoplasm, nucleus, membranes (including the plasmalemma, nuclear membrane, endoplasmic reticulum or other internal membrane compartments), in organelles (including the mitochondria, peroxisome, lysosome, endosome or other organelles), or secreted. Those proteins may function as intracellular or extracellular structural elements, ligand, hormones, neurotransmitter, growth regulating factors, differentiation factors, gene-expression regulating factors, DNA-associated proteins, enzymes, serum proteins, receptors, carriers for small molecular weight organic or inorganic compounds, drugs, immunomodulators, oncogenes, tumor suppressor, toxins, tumor antigens, or antigens. These proteins may have a natural sequence or a mutated sequence to enhance, inhibit, regulate, or eliminate their biological activity. A specific example of a protein to be expressed is hGHRH.

In addition, the nucleic acid cassette can code for RNA. The RNA may function as a template for translation, as an antisense inhibitor of gene expression, as a triple-strand forming inhibitor of gene expression, as an enzyme (ribozyme) or as a ligand recognizing specific structural determinants on cellular structures for the purpose of modifying their activity. Specific examples include RNA molecules to inhibit the expression or function of prostaglandin synthase, lipo-oxenganse, histocompatibilty antigens (class I or class II), cell adhesion molecules, nitrous oxide synthase, $\beta_2$ microglobulin, oncogenes, and growth factors.

The compounds which can be incorporated are only limited by the availability of the nucleic acid sequence for the protein or polypeptide to be incorporated. One skilled in the art will readily recognize that as more proteins and polypeptides become identified they can be integrated into the vector system of the present invention and expressed in animal or human tissue.

Transfection can be done either by in vivo or ex vivo techniques. For example, muscle cells can be propagated in culture, transfected with the transforming gene, and then transplanted into muscle tissue. Alternatively, the vectors can be administered to the cells by the methods discussed above.

Methods of Use

A. Treatment with Growth Hormone Releasing Hormone

Growth hormone is normally produced and secreted from the anterior pituitary and promotes linear growth in prepuberty children. Growth hormone acts on the liver and other tissues to stimulate the production of growth hormone releasing hormone. This factor is, in turn, responsible for the growth promoting effects of growth hormone. Further, this factor serves as an indicator of overall growth hormone secretion. Serum IGF-I concentration increases in response to endogenous and exogenous administered growth hormone. These concentrations are low in growth hormone deficiency.

Growth hormone releasing hormone is one of the key factors that potentiates muscle development and muscle growth. Myoblasts naturally secrete GHRH as well as its cognate binding proteins during the onset of fusion. This process coincides with the appearance of muscle specific gene products. In terminally differentiated muscle, signals propagated from passive stretch induced hypertrophy induce the expression of IGF genes. Many of the actions of IGFs on muscle result from interactions with the GHRH receptor.

The intramuscular injection of an expression vector containing the sequence for GHRH (for example, pSK-GHRH) can be used to treat growth disorders. Vectors are designed to preferably control the expression of GHRH in a range of 0.1–10 ng/ml. Since intramuscular expression of vectors leads to expression of the product encoded by the nucleic acid cassette for several months, this method provides a long-term inexpensive way to increase systemic blood concentration of GHRH and consequently GH and IGF-I in patients with growth hormone deficiency.

B. Treatment of Muscle Atrophy Due To Age

Growth hormone levels decline with increasing age. The levels in healthy men and women above age of 55 are approximately one third lower than the levels in men and women 18 to 33. This is associated with a decrease in the concentration of IGF-I. The decline in growth hormone and IGF-I production correlate with the decrease in muscle mass, termed senile muscle atrophy, and increase in adiposity that occur in healthy human subjects. Administering growth hormone three times a week to healthy 61 to 81 year old men who had serum levels below those of healthy younger men increased the serum IGF-I levels to within the range found in young healthy adults. This increased level led to increased muscle mass and strength and reduced body fat. The secretion of growth hormone is regulated by a stimulatory (growth hormone releasing hormone) and an inhibitory (somatostatin) hypothalamic hormone.

The convenient cloning sites in the expression vectors of the present invention are used to construct vectors containing human growth hormone CDNA sequence, the human growth hormone releasing hormone (GHRH), or IGF-I. This versatility is important since the GHRH, GH, and IGF-I, while having similar desired effects on muscle mass, may have different side effects or kinetics which will affect their efficacy. The expression of the growth hormone releasing hormone might be more advantageous than the expression of either IGF-I or the growth hormone vectors transcripts. Since GHRH is reduced in the elderly it appears to be responsible for the lack of GH secretion rather than the anterior pituitary capability of synthesizing growth hormone, thus the increased expression of GHRH from muscle would increase GHRH levels in the systemic blood system and can allow for the natural diurnal secretion pattern of GH from the anterior pituitary. In this way, GHRH could act as the natural secretogogue, allowing for elevated secretion or release of GH from the hypothalamus of the elderly.

Thus, the application of vector systems described herein to express growth hormone releasing hormone through the injection of the pSK-GHRH or related vectors, vectors expressing HG, or IGF-I into adult muscle of the elderly is a long-term inexpensive way to increase systemic blood concentration of IGF-I in the elderly.

Administration of the vectors can be intravenously, through direct injection into the muscle or by any one of the methods described above. Dosages will depend on the severity of the disease and the amount of dosage is readily determinable by standard methods. The duration of treatment will extend through the course of the disease symptoms which can be continuously.

C. Treatment of Osteoporosis

Osteoporosis is a common accelerated loss of bone mass that often accompanies aging. The decreased bone density associated with osteoporosis leads to an increased susceptibility to bone fractures. Treatment with IGF-I is associated with increased bone density. Thus, administration of a vector encoding GHRH to muscles by direct injection or hypospray will induce a higher level of IGF-I production and will thereby aid in the redeposition of bone and thereby decrease the risk of fractures.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

D. Treatment of Cachexia

Muscle wasting (cachexia, negative nitrogen balance, loss of lean body mass) is a common complication of a number of chronic diseases, such as AIDS, cancer, and rheumatic disease. This process contributes substantially to a morbid cycle of inactivity, malnutrition , and opportunistic infections, resulting in prolonged disability, extended hospitalization, and considerable health care expense. Muscle wasting is also a common feature of morbid ageing and it is likely that measures to preserve muscle mass would have a substantial beneficial impact in the morbidly ageing population. Reversal of muscle wasting may be an efficient method for treating osteoporosis as well.

Current therapies focus on dietary management with the use of high calorie dietary supplements or parenteral nutrition or use of appetite stimulants. Dietary approaches are inherently limited by the poor utilization of caloric intake in these patients. Androgens are theoretically effective but have profound side effects which complicate their use. Thus, there is a need for an effective medicinal approach which directly promotes preservation of muscle mass. Preferably the approach will involve a therapeutic composition which does not require frequent administration, thus providing improved compliance in chronically ill and ageing populations.

IGF-1 is the major growth factor promoting the differentiation of muscle cells and increasing muscle mass. Studies in animals demonstrate that IGF-1 will effectively reverse cachexia, though this requires chronic (ideally continuous) administration. hGH has also been shown to preserve lean body mass in animal studies and is in use in many clinical trials for this indication.

The stimulation of GH and IGF-1 for the treatment of cachexia can advantageously be provided by the in vivo expression of GHRH from a vector, e.g., the pSK-GHRH vector, thereby avoiding the difficulties associated with direct administration of IGF-1 or GH. This method is expected to be particularly advantageous in cases of systemic muscle wasting. The vector can be administered by various methods, such as those indicated above. An example of such an administration method is the direct injection of a composition containing the vector encoding GHRH in muscle tissue of the patient to be treated.

Improvement of Livestock

An additional embodiment of the present invention is the improvement of livestock by injection of GHRH vector constructs, or similar constructs encoding other growth hormones, such as growth hormone or growth hormone releasing hormone. It has been shown that GHRH stimulates milk production (galactopoietic) with no alteration in milk composition, and sustains growth, mostly on the behalf of lean body mass, in farm animals (Enright et al., 1993, *J. Animal Science* 71:2395–2405; Enright et al., 1986, *J. Dairy Science* 69:344–351). Thus, muscle injection of vectors encoding GHRH by hypodermic or hypospray administration will promote increased muscle mass and reduced body fat in important livestock species such as cattle, sheep, swine, rabbits, deer, fish and birds such as turkeys, chickens, ducks, and geese. Likewise, milk production can also be stimulated by in vivo expresssion of GHRH from vectors such as those described above. Administration of the vectors can also be through any one of the methods described above.

The following examples are offered by way of illustration and are not intended to limit the invention in any manner.

EXAMPLE 1

Construction of pSK-GHRH and pSK-LacZ

The plasmid DNA backbone was pBlueScript KS+ (pBS). In order to construct hybrid pSK-GHRH, a 448 bp fragment (−424/+24) of avian skeletal α-actin promoter (SK) (Lee, T. C. et al., *Oncogene* 9:1047–1052 (1994); Chow, K. L. et al., *Proc. Natl. Acad. Sci. USA*, 88:1301–1305 (1991)) was cloned upstream from the hGHRH cDNA 228 bp fragment (part of exon 2, all exon 3 and part of exon 4) coding for the 31 amino acid signal peptide and entire mature hGHRH1-44 peptide (Tyr1→Leu44) inserted into the BamHI/HindIII sites of pBS derived plasmid. The 3' untranslated region of hGH cDNA in a 622 bp SmaI/EcoRI blunted fragment, was excised from the commercial pOGH plasmid (Nichols Institute) and cloned into blunted-ended ClaI/EcoRI sites of pBS derived plasmid. In the pSK-LacZ construct, the β-galactosidase gene of *Escherichia coli*, with a nuclear localization signal (nls), is driven by the same SK promoter, but contains the 3'UTR of skeletal α-actin gene.

EXAMPLE 2

In Vitro Expression of pSK-GHRH

A plasmid vector which is capable of directing high-level gene expression in a skeletal muscle specific manner is generated as follows. A 228 bp fragment of hGHRH, which encode for the 31 amino acid signal peptide and the entire mature peptide hGHRH(1-44)OH (Tyr1→Leu44), was cloned into a pBS-derived vector. Gene expression was controlled by a 448 bp fragment (−424/+24) of the avian skeletal α-actin gene, which contains several evolutionarily conserved regulatory elements that accurately initiate skeletal α-actin transcripts and drives transcription of a variety of reporter genes specifically in differentiated skeletal muscle cells. The GHRH coding region was followed by the 3' untranslated region of human growth hormone cDNA.

EXAMPLE 3

In Vitro Expression of pSK-GHRH

Figure 12:
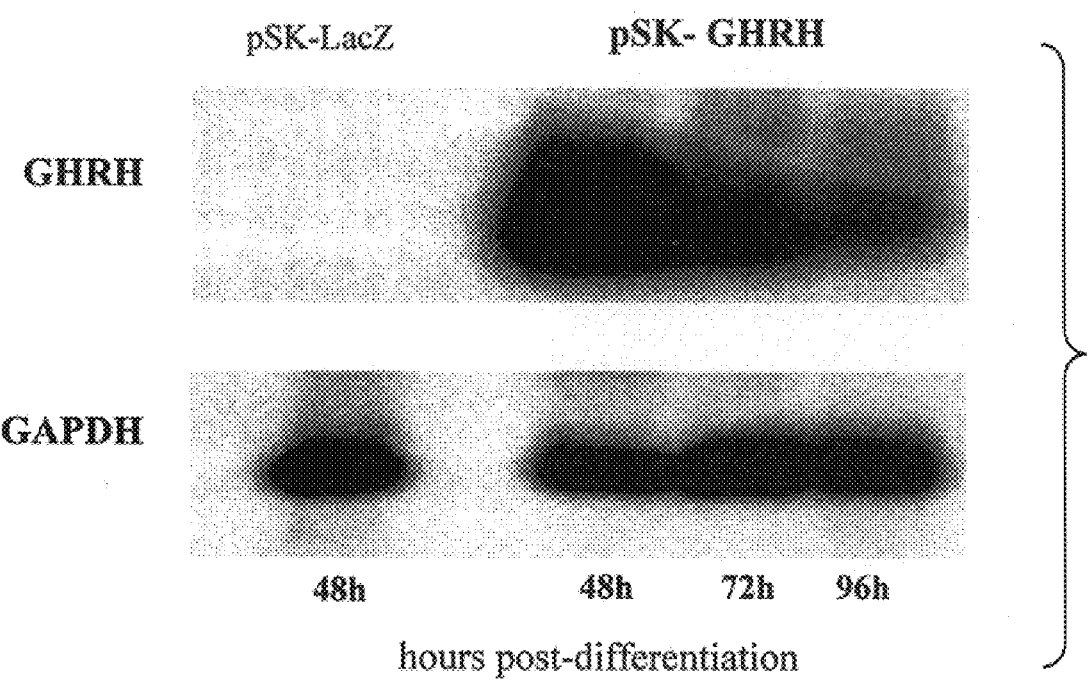
FIG. 12 shows a Northern blot analysis of chicken primary myoblast culture transiently transfected with pSK-GHRH or pSK-LacZ, as a control. 10μ of total RNA were separated, transferred onto a nylon membrane and hybridized with a hGHRH cDNA probe and then with a mouse GAPDH probe in order to normalize the results.

In vitro expression of pSK-GHRH was examined in transiently transfected chicken primary myoblasts. pSK-GHRH and pSK-LacZ transfected cells were placed into differentiation media for 24–72 h to initiate withdrawal from the cell cycle and to induce post-fusion differentiation. The media was changed to a minimal serum-free media for a 24 h pulse. Cells were harvested 48 to 96 h post-differentiation. Northern blot analysis (FIG. 12) showed the expected size transcripts of 0.35 kb, in myoblasts transfected with pSK-GHRH, but not in pSK-LacZ transfected myoblasts. The expression of pSK-GHRH peaked at 48 h post-differentiation and was reduced thereafter in comparison to the glycolytic enzyme GAPDH. This pattern of activation is characteristic for chicken skeletal α-actin promoter, which induces high levels of transgene expression in myotubes but not in replicating myoblasts.

Conditioned serum-free media from PSK-GHRH and pSK-LacZ transfected myoblasts were collected and purified on C18 Sep-Columns, which served to separate the peptide to be assayed from potentially interfering substances and to concentrate the samples to determine levels of radioimmunoassayable hGHRH. Chicken primary myoblasts transfected with pSK-GHRH produced approximately 1.7 ng hGHRH(1-44)OH/million cells/h.

EXAMPLE 4

In Vitro Activity of pSK-GHRH

The in vitro potency of the hGHRH (1-44)OH molecule secreted by primary pig myoblasts (ppm) transiently transfected with pSK-GHRH was compared to that of the hGHRH (1-44)$NH_2$ synthetic molecule for its ability to stimulate GH release from primary pig anterior pituitary cells after a 24 h stimulation at 37° C. GH release from the primary pig anterior pituitary cells rose from values of 7±2 ng/ml to 82.5±3.1 ng/ml ($p \leq 0.002$) when stimulated with 5 ml culture media from 1 million primary pig myoblasts transiently transfected with pSK-GHRH, containing a radio-immunoassay equivalent estimated to be 10 ng of hGHRH (1-44)OH. This value equals 72% of that obtained when the pituitary cells were stimulated with myoblast serum-free media mixed with 10 ng synthetic hGHRH (1-44)$NH_2$ then purified and processed as the test media (GH release in this case was 115±3.2 ng/ml). Thus, hGHRH(1-44)OH secreted by skeletal pig myocytes transfected with pSK-GHRH retain functional activity in pig pituitary cell culture and induces secretion of significant levels of GH. This is an important finding, and contracts with prior art technique. Pig (1-44) GHRH, as well as the human molecule, is amidated, while the molecule which is expressed by the present construct is non-amidated at amino acid 44.

EXAMPLE 5

In Vivo Expression and Activity of pSK-GHRH

On day 0, animals were anesthetized and injected with 100μ of pSK-GHRH of pSK-LacZ in 100μ PBS into the regenerating quadriceps muscle. The animals were killed over the next 3 weeks and samples of the injected muscles were collected and frozen in liquid nitrogen and blood collected by transcardiac puncture.

Figure 13:
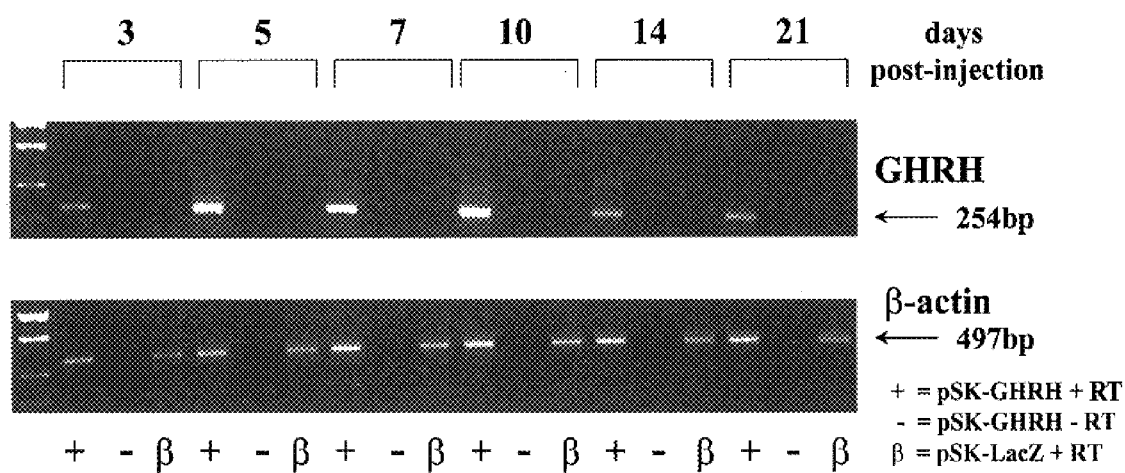
FIG. 13 shows expression of pSK-GHRH assessed by RT-PCR at 3–21 days after i.m. injection of 100μ pSK-GHRH into the regenerating left quadriceps muscle of adult C57/B16 mice. RT-PCR reaction from 1 g of total RNA—upper panel: 254 bp PCR fragment using SK-GHRH cDNA specific oligonucleotides; lower panel: 497 bp PCR fragment using mouse cytoskeletal β-actin cDNA specific oligonucleotides, in pSK-GHRH injected animals or pSK-LacZ injected animals.

The in vivo expression of PSK-GHRH was assessed by RT-PCR on injected muscle (FIG. 13). Muscle RNA was DNase I treated in order to eliminate the injected plasmid, reextracted and 1 mg of total RNA was used in the reverse transcriptase reaction. Only the pSK-GHRH injected muscles showed a 254 bp PCR fragment when amplified with GHRH specific primers ([+]pSK-GHRH). The pSK-LacZ injected muscles showed a 497 bp PCR fragment for mouse cytoskeletal β-actin, used as a control, but not for GHRH. The efficiency of DNase treatment to eliminate plasmid DNA was screened by using RNA from pSK-GHRH injected muscle: when the reverse transcriptase was omitted from the reaction, no amplification was observed ((−) pSK-GHRH).

Figure 14:
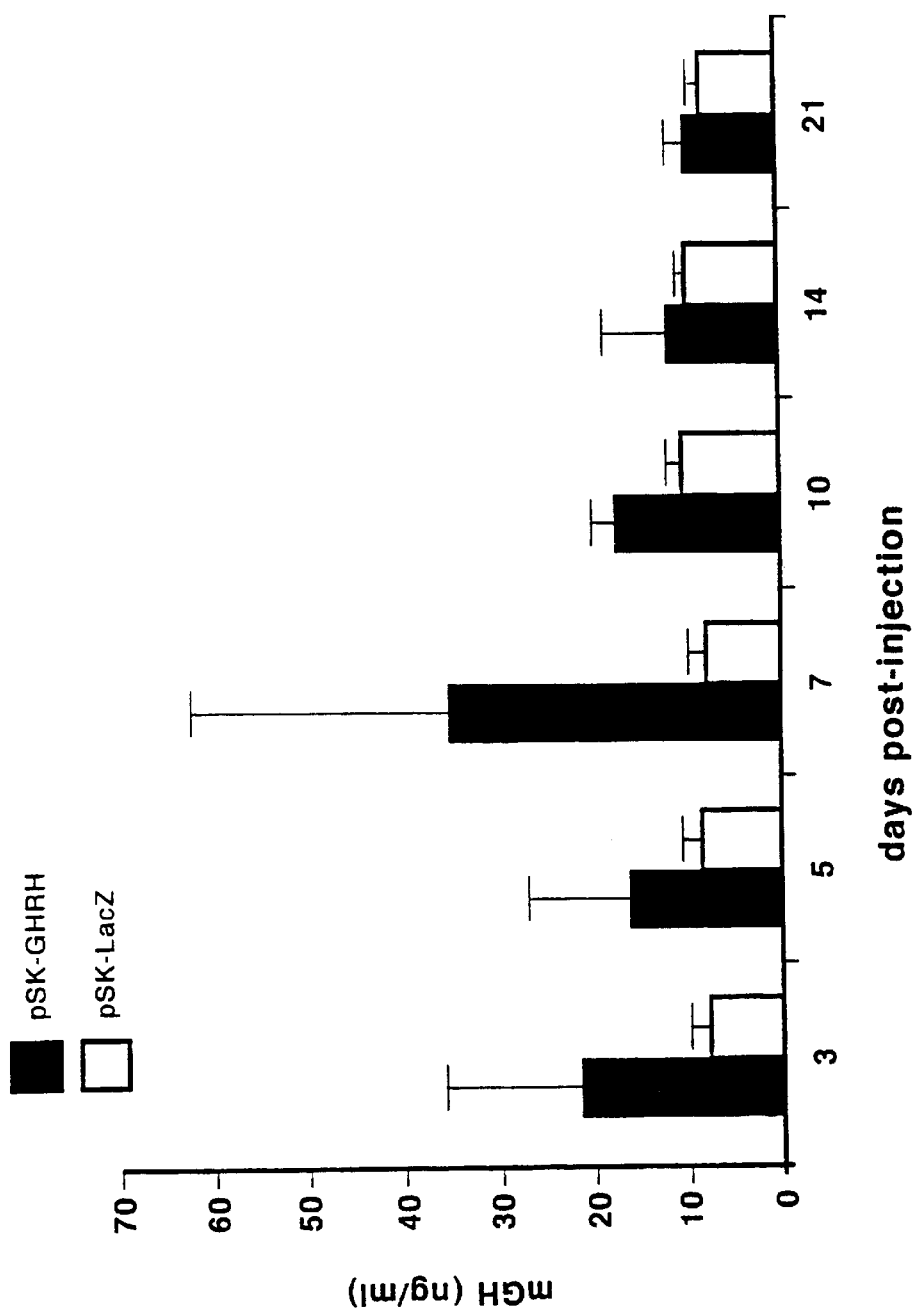
FIG. 14 shows mouse serum growth hormone was measured by rat GH heterologous radioimmunoassay after i.m. injection of 100μ pSK-GHRH in adult C57/B16 mice. Control sera were obtained from mice injected with pSK-LacZ. The results are presented as means±s.e.m. Significant differences of *, p≦0.03 and p≦0.05 were obtained at day 7 and day 10, respectively.

Serum mGH in the PSK-GHRH injected animals was significantly elevated as compared to the mGH levels in serum from control mice (FIG. 14). Time course analysis of mGH as a response to pSK-GHRH injections showed stimulation at 3 days post-injection (21.54±15.29 ng/ml vs. 7.53±0.57 ng/ml, n=6), peaked at 7 days post-injection (36.28±27.28 ng/ml vs. 8.2±1.9 ng/ml, $p \leq 0.05$, n=6) and declined gradually to the base-line by 21 days post-injection (9.16±2.54 ng/ml vs. 6.76±0.89 ng/ml, n=6).

Figure 15:
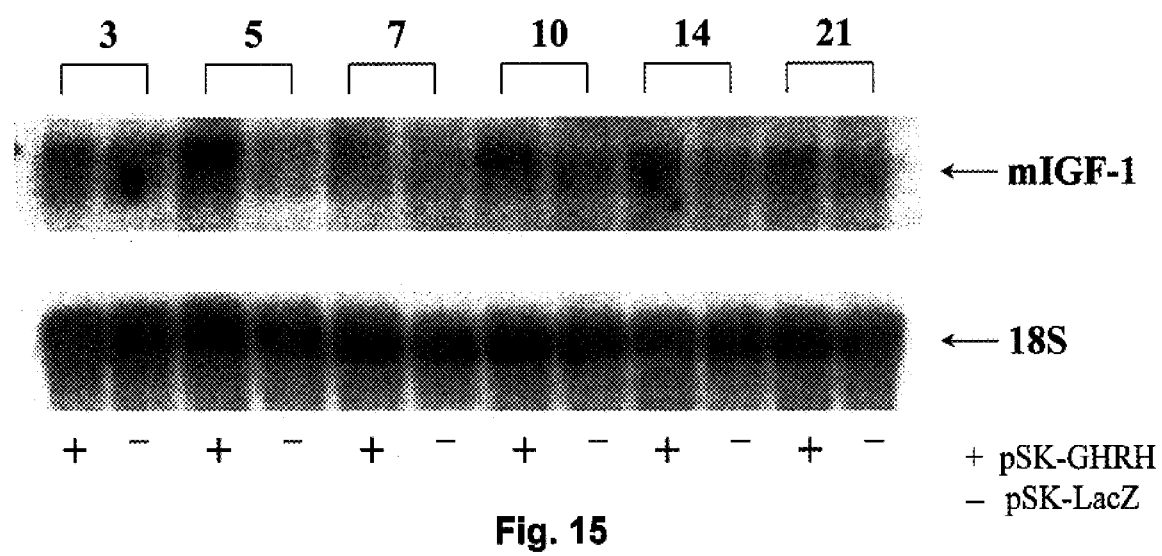
FIG. 15 shows Northern blot analysis of mouse liver RNA in PSK-GHRH (+) or pSK-LacZ (−) injected animals. The animals were killed and livers harvested at day 3–21, 20μ of total RNA was separated, transferred onto a nylon membrane and hybridized with an mIGF-1 cDNA probe and then a mouse 18S probe in order to normalize the results.
Figure 16:
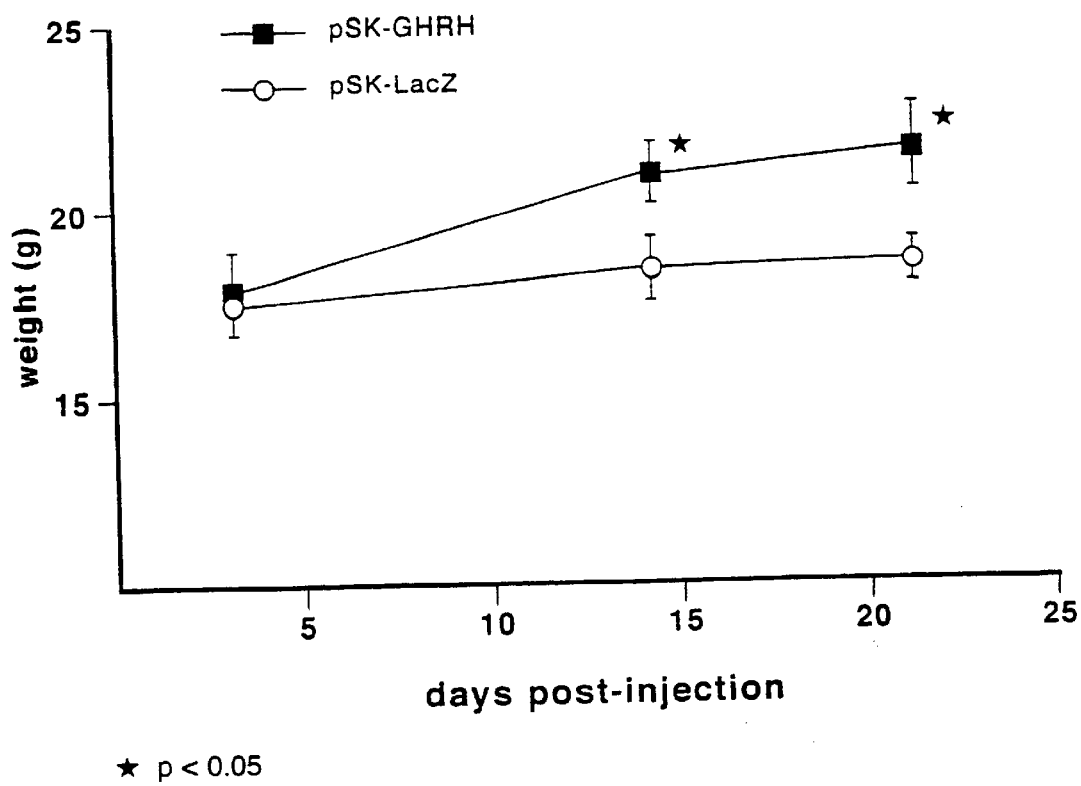
FIG. 16 shows increased gain in body weight after a single injection of pSK-GHRH in the regenerating left quadriceps muscle of adult mice. pSK-GHRH (black, n=6) are compared to that of age-matched pSK-LacZ injected animals (white, n=6). The results are presented as means±s.e.m. * p≦0.05 and p≦0.03, was observed at day 14 and day 21, respectively.

Another indication of increased systemic levels of GH would be elevated IGF-1 biosynthesis in the liver. Thus, liver IGF-1 expression of injected mice and controls was evaluated by Northern blot analysis of total RNA (FIG. 15). Elevated mIGF-1 mRNA expression was detected in all pSK-GHRH injected animals in comparison to a relatively stable baseline of IGF-1 RNA in pSK-LacZ injected mice. IGF-1 mRNA levels increased within 3 days post-injection and was maintained up to 21 days.

hGHRH secreted into the systemic circulation after intramuscular injection of pSK-GHRH enhanced growth in normal mice (FIG. 16), as shown by significant differences in their total body mass at 14 days (21.11±1.47 g vs. 18.62±0.4 g, $p \leq 0.043$) and 21 days (21.86±1.45 g vs. 18.8±0.42 g, $p \leq 0.028$) after a single injection of pSK-GHRH. These results demonstrate that the i.m. injection of pSK-GHRH can be used to produce physiological levels of GHRH in the circulation of adult animals.

Figure 17:
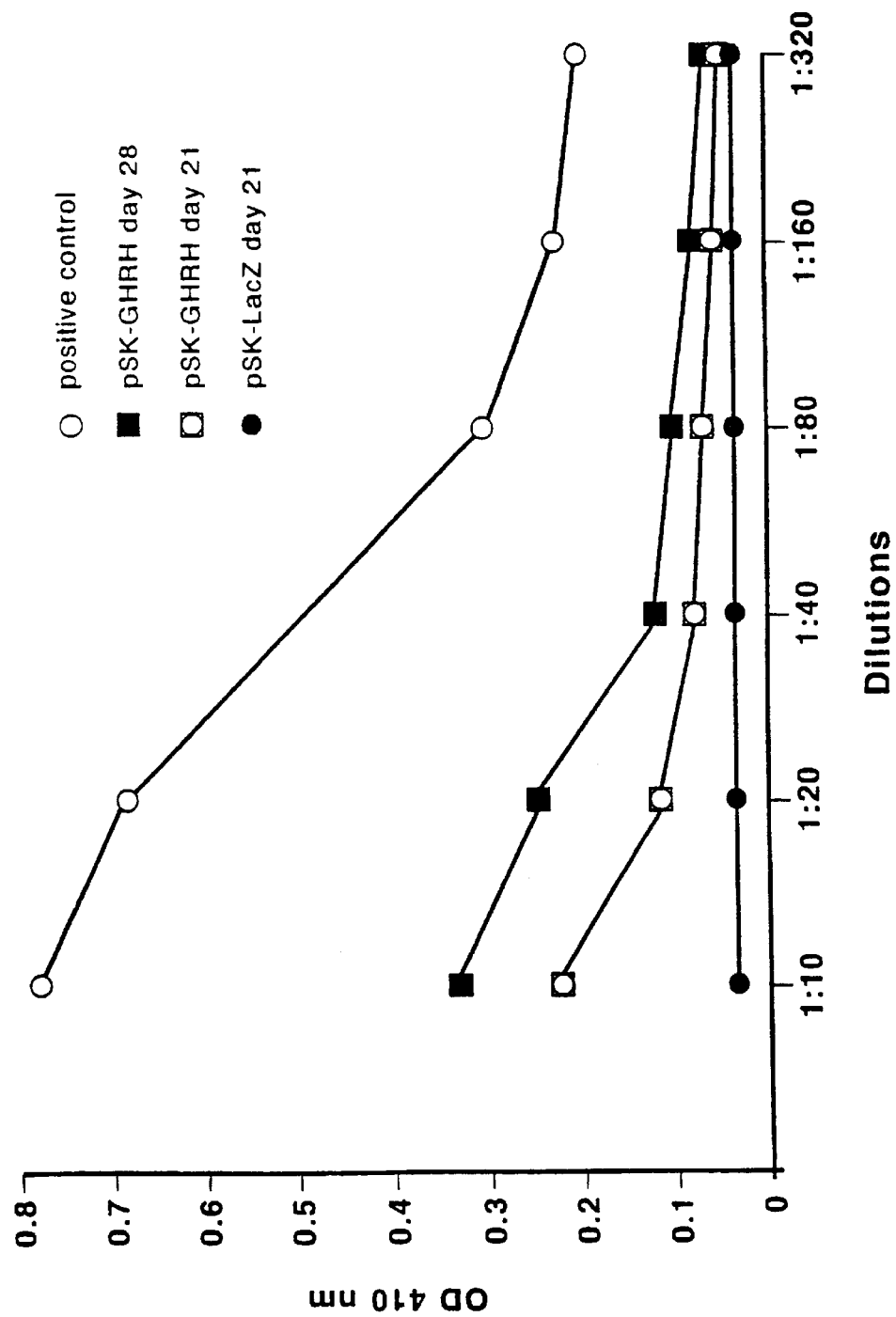
FIG. 17 shows generation of mouse anti human GHRH antibodies following intramuscular injection of pSK-GHRH in C57/B16 mice. 21 (n=3) and 28 (n=3) days after injection of pSK-GHRH and 21 days after pSK-LacZ (n=3) injections, serial dilutions of sera were assayed for anti-GHRH antibodies by ELISA. A significant difference, p≦0.05 was observed between pSK-GHRH injected mice and control curves.

However, the hGHRH is unsuitable for use in other animals. Only a transient increase was observed in mGH in vivo, after i.m. injection of PSK-GHRH in adult mice. This response is due to a humoral immune response targeted against hGHRH, which is a heterologous protein in mouse. The antibody response to hGHRH was demonstrated using an ELISA assay (FIG. 17). Antibodies to hGHRH were detected in sera collected 21 days and 28 days after intramuscular injection of pSK-GHRH but not in sera collected 21 days after intramuscular injection of pSK-LacZ (p±0.05). Also, the persistence of hGHRH transcripts in the muscle 21 days after injection demonstrate that expression persists and that the decline of serum hGHRH concentrations is due to the humoral immune response.

Cloning the cDNA coding for the hGHRH(1-40)OH molecule, which is naturally/hydroxylated and has the same potency in vivo as hGHRH(1-44)NH$_2$ provides greater GH release in plasmid injected animals. In addition, mutation of some of the amino acids which are known to be sites for different peptidases, prolong the half-life of the hGHRH molecule. In order to regulate the expression level in vivo and to obtain, if necessary, a discontinuous release of GHRH, a gene switch (Wang, Y. et al., *Nature Biotechnology* 15:239–243 (1997)) is an important element to be added.

The lost cost, the possibility of large scale production of plasmid DNA, combined with the easy administration procedure and the 10–20 times higher potency at the same dose as compared to GH, provides utility for agricultural uses. The intramuscular plasmid delivery represents a practical way to improve performance of domestic animals and provide an alternative to classical GH treatments.

A GHRH plasmid delivery, which avoids the frequent administration of recombinant proteins currently used in agriculture and human clinics and provides a more natural alternative for the GH-based therapies.

EXAMPLE 6

Cell Culture

Minimal Essential Medium (MEM), heat inactivated horse serum (HIHS), gentamicin, Hank's Balanced Salt Solution (HBSS), lipofectamine were obtained from Gibco BRL. The skilled artisan recognizes that primary chicken myoblast cultures can be obtained (Bergsma, D. J. et al., *Molecular & Cellular Biology* 6:2462–2475 (1986)). Cells were plated 24 h prior to transfection at a density of 1.5 million cells/100 mm plate, in MEM supplemented with 10% HIHS, 5% chicken embryo extract (CEE) and gentamicin. Cells were maintained in a humidified 5% $CO_2$ 95% air atmosphere at 37° C. Cells were transfected with 4μ of pSK-GHRH or pSK-LacZ per plate using lipofectamine, according to the manufacturer instructions. After transfection, the medium was changed to MEM which contained 2% HIHS, 2% CEE for at least 24 h to allow the cells to differentiate. Primary pig myoblast cultures were obtained as described in Doumit, M. E. et al., *Tissue & Cell* 24:253–262 (1992). Cells were plated at a density of 1 million cells/100 mm plate and maintained in growth media for 2–3 days. The cells were passed for 2 times prior to transfection. Porcine myoblast cultures were transfected and differentiated under the same conditions as the primary chicken myoblast cultures. Media and cells were harvested 48, 72 and 96 h postdifferentiation. The samples and controls were assayed in quadruplicate. The efficiency of transfection was estimated by β-galactosidase histochemistry of control plates to be 10%. One day before harvesting, cells were washed twice in HBSS and the media changed to MEM, 0.1% BSA. The cells were homogenized directly into Ultraspec RNA reagent (Biotecx Laboratories) for the isolation of total RNA. Conditioned media was treated by adding 0.25 volume of 1% triflouroacetic acid (TFA) and 1 mM phenylmethylsulfonylflouride (PMSF), frozen at −80°, lyophilized, purified on C-18 Sep-Columns, relyophilized and used in RIA or resuspended in media conditioned for primary pig anterior pituitary culture. The pit anterior pituitary culture was obtained as described (Tanner, J. W. et al., *J. Endocrinol* 125:109–115 (1990)). Pig GH was assayed as described in Barb, C. R. et al., *Domestic Animal Endocrinology* 8:117–127 (1991).

EXAMPLE 7

Northern Blot Analysis

10–20μ of total RNA was DNase I treated (Gibco BRL), size separated in 1.5% agarose-formaldehyde gel and transferred to Gene Screen nylon membrane (DuPont Research Products). The membranes were hybridized with cDNA probes $^{32}$P labeled by random priming (Ready-to-Go DNA labeling kit, Pharmacia Biotech). Hybridization was carried out at 45° C. in a solution which contained 50% formamide, 5×SSPE, 5×Denhardt's, 1% SDS, 200 mg/ml sheared salmon sperm DNA. Membranes were washed twice for 10 minutes in 2×SSPE/1%SDS at room temperature and twice for 30 minutes in 0.2×SSPE/1%SDS at 68° C. Blots were subsequently exposed to X-ray film (Kodak X-Omat AR) at −80° C. with intensifying screens.

EXAMPLE 8

Intramuscular Injection of Plasmid DNA in Adult Mice

C57/B16 male mice (Taconic Laboratories) were housed under environmental conditions of 10 h light/14 h darkness. On day −5, the left quadriceps muscle of mice (17–20 g body weight) was injected with 50 g of 0.75% bupivacaine hydrochloride in saline solution. On day 0 the animals were weighed, the regenerating muscle was exposed and injected with 100$\mu$ PBS. The animals were weighed and killed 3–21 days later. Blood was collected, centrifuged immediately at 0° C., and stored at −80° C. prior to analysis. Injected and control organs were removed and frozen in liquid nitrogen.

EXAMPLE 9

RT-PCR

Muscle RNA was extracted with Ultraspec RNA reagent. 1$\mu$ of total RNA was treated twice with 10 units of DNase I (Gibco BRL) and phenol-chloroform extracted. RNA pellets were resuspended in 20$\mu$ DEPC-water. Reverse transcriptase reactions were performed with the SuperScript Preamplification System for First Strand cDNA Synthesis (Gibco BRL) according to manufacturer instructions. In (−) pSK-GHRH tubes the reverse transcriptase was omitted. Specific oligonucleotide primers were used to amplify either a 254 bp fragment of pSK-GHRH cDNA: 5'TGGT-GCTCTGGGTGTTCTT3' (sense) (SEQ ID NO.12) and 5'GCTTGATATCGAATTCCTGC3' (anti-sense) (SEQ ID NO.13) or a 497 bp control fragment of mouse cytoskeletal β-actin cDNA: 5'TCAGAAGGACTCCTATGTGG3' (sense) (SEQ ID NO.14) and 5'TCTCTTTGATGTCACGCACG3' (anti-sense) (SEQ ID NO.15). The PCR conditions were, 32 cycles (94° C. for 30 s, 60° C. for 30 s, 72° C. for 1 min) in 50$\mu$ containing 5$\mu$ of final volume of RT reaction diluted in 1×PCR buffer which contained 1.5 mM MgCl$_2$, 200 mM each dNTP, 2.5 units AmpliTaq DNA polymerase (Perkin-Elmer) and 100 ng of each specific primer.

EXAMPLE 10

Mouse Growth Hormone RIA

Mouse GH in plasma was measured with a heterologous rat assay system (Amersham). The sensitivity of the assay was 0.16 ng/tube. The intra- and interassay coefficients of variation were 6.5 and 6.8% respectively.

EXAMPLE 11

Detection of Mouse anti-hGHRH Antibodies

Mouse anti-hGHRH antibodies were detected by ELISA. Ninety-six-well plates (Dynatech Laboratories) were coated with 500 ng of purified of hGHRH (Peninsula Laboratories) per well (in HEPES buffered saline) at 4° C. overnight. The wells were washed five times with PBS, blocked with PBS containing 5% (w/v) non fat dry milk and then incubated 2 hours at room temperature with serial dilutions of serum (in PBS+2%BSA) from pSK-GHRH or pSK-LacZ injected mice. The wells were washed five times with PBS and then incubated with 50 ml of a 1:2000 dilution of HRP-conjugated goat anti-mouse IgG for 2 hours at room temperatures. 200$\mu$ of peroxidase developing reagent (ABTS substrate) were incubated for 1 hour at room temperature. Plates were read at 410 nm in a Dynatech MR600 plate reader. In this assay, a rabbit anti-hGHRH antibody used with a HRP-conjugated goat anti-rabbit seondary antibody was the positive control for sensitivity.

EXAMPLE 12

Statistics

Date were analyzed using Microsoft Excel statistics analysis package. Specific p values were obtained by comparison using Student's t test. A value of p≦0.05 was taken to be statistically significant. Values shown in the figures are the mean ±s.e.m.

TABLE 1

Mouse growth hormone values in pSK-GHRH injected mice and controls (ng/ml)

|  | GH | LacZ | AvGHRH | AvLacZ |
| --- | --- | --- | --- | --- |
| day 3 | 6.8 | 7.2 | 16.45 | 7.45 |
|  | 9 | 8.2 |  |  |
|  | 12 | 6.2 |  |  |
|  | 38 | 8.2 |  |  |
| day 5 | 11 | 7.8 | 17.5 | 8.9 |
|  | 24 | 10 |  |  |
| day 7 | 12 | 7.2 | 42.5 | 9.25 |
|  | 70 | 10 |  |  |
|  | 28 | 12 |  |  |
|  | 60 | 7.8 |  |  |
| day 10 | 17 | 12.4 | 17.5 | 10.2 |
|  | 18 | 8 |  |  |
| day 14 | 17 | 7.5 | 11.9 | 8.8 |
|  | 5.6 | 7.4 |  |  |
|  | 17.6 | 12 |  |  |
|  | 7.4 | 8.3 |  |  |
| day 21 | 9 | 6.2 | 9.4 | 6.766667 |
|  | 6.2 | 6.3 |  |  |
|  | 13 | 7.8 |  |  |

TABLE II

Identification of GHRH Sequences

SEQ ID NO. 5 Bovine growth horinone releasing hormone sequence

Tyr Ala Asp Ala Ile Phe Thr Asn Ser Tyr Arg Lys Val
1              5                   10
Leu Gly Gln Leu Ser Ala Arg Lys Leu Leu Gln Asp Ile
        15              20                  25
Met Asn Arg Gln Gln Gly Glu Arg Asn Gln Glu Gln Gly
            30                  35
Ala Lys Val Arg Leu
40

SEQ ID NO. 6 Porcine growth hormone releasing hormone sequence

Tyr Ala Asp Ala Ile Phe Thr Asn Ser Tyr Arg Lys Val
1              5                   10
Leu Gly Gln Leu Ser Ala Arg Lys Leu Leu Gln Asp Ile
        15              20                  25
Met Ser Arg Gln Gln Gly Glu Arg Asn Gln Glu Gln Gly
            30                  35
Ala Arg Val Arg Leu
40

SEQ ID NO. 7 Ovine growth hormone releasing hormone sequence

Tyr Ala Asp Ala Ile Phe Thr Asn Ser Tyr Arg Lys Ile
1              5                   10
Leu Gly Gln Leu Ser Ala Arg Lys Leu Leu Gln Asp Ile
        15              20                  25
Met Asn Arg Gln Gln Gly Glu Arg Asn Gln Glu Gln Gly
            30                  35
Ala Lys Val Arg Leu
40

SEQ ID NO. 8 Mouse growth hormone releasing hormone sequence

His Val Asp Ala Ile Phe Thr Thr Asn Tyr Arg Lys Leu
1              5                   10
Leu Ser Gln Leu Try Ala Arg Lys Val Ile Gln Asp Ile
        15              20                  25
Met Asn Lys Gln Gly Glu Arg Ile Gln Glu Gln Arg Ala
            30                  35
Arg Leu Ser
40

SEQ ID NO. 9 Caprine growth horrnone releasing hormone sequence

Tyr Ala Asp Ala Ile Phe Thr Asn Ser Tyr Arg Lys Val
1              5                   10
Leu Gly Gln Leu Ser Ala Arg Lys Leu Leu Gln Asp Ile
        15              20                  25
Met Asn Arg Gln Gln Gly Glu Arg Asn Gln Glu Gln Gly
            30                  35
Ala Lys Val Arg Leu
40

SEQ ID NO. 10 Human 1–40 OH growth hormone releasing hormone sequence

Tyr Ala Asp Ala Ile Phe Thr Asn Ser Tyr Arg Lys Val
1              5                   10
Leu Gly Gln Leu Ser Ala Arg Lys Leu Leu Gln Asp Ile
        15              20                  25
Met Ser Arg Gln Gln Gly Glu Ser Asn Gln Glu Arg Gly
            30                  35
Ala
40

SEQ ID NO. 11 Mouse porcine chimeric growth hormone releasing hormone sequence His Val Asp Ala Ile Phe Thr Thr Asn Tyr Arg Lys Leu
1              5                   10
Leu Ser Gln Leu Ser Ala Arg Lys Leu Leu Gln Asp Ile
        15              20                  25
Met Ser Arg Gln Gln Gly Glu Arg Asn Gln Glu Gln Gly
            30                  35
Ala Arg Val Arg Leu
40

)

One skilled in the art will readily appreciate that the present invention is well adapted to carry out the objects and obtain the ends and advantages mentioned as well as those inherent therein. The vector systems along with the methods, procedures treatments and vaccinations described herein are presently representative of preferred embodiments are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein within departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A vector for expression of a nucleic acid sequence in a cell, comprising:
   a nucleic acid cassette comprising a nucleotide sequence encoding a growth hormone releasing hormone ("GHRH");
   a 5' flanking region including one or more sequences necessary for expression of said nucleic acid cassette, wherein said sequences include a promoter,
   a linker nucleic acid sequence linking said 5' flanking region to a nucleic acid, said linker nucleic acid sequence comprising a site for inserting said nucleic acid cassette, wherein said linker nucleic acid sequence lacks the coding sequence of a gene with which it is naturally associated; and
   a 3' flanking region operably linked to said linker nucleic acid sequence, wherein said 3' flanking region comprises a 3' untranslated region ("UTR") or a 3' noncoding region ("NCR") or both, wherein said 3' flanking region is 3' to said site for inserting said nucleic acid cassette, wherein said nucleotide sequence encoding said GHRM is a synthetic sequence encoding a human GHRH wherein said human GHRH has the sequence of SEQ ID NO: 2.

2. The vector of claim 1, wherein said promoter is a promoter from a skeletal α-actin gene.

3. The vector of claim 2, wherein said promoter is from a chicken skeletal α-actin gene.

4. The vector of claim 2, wherein said promoter is from a human skeletal α-actin gene.

5. The vector of claim 1, wherein said 3'-UTR is a growth hormone 3'-UTR.

6. The vector of claim 5, wherein said growth hormone 3'-UTR is from a human growth hormone gene.

7. The vector of claim 5, wherein an ALU repeat or ALU repeat-like sequence is deleted from said 3'UTR.

8. The vector of claim 1, wherein said GHRH is human GHRH, said promoter is from a chicken skeletal α-actin gene, and said 3'-UTR is from a human growth hormone gene.

9. The vector of claim 1, wherein said 5' flanking region or said 3' flanking region or both regulates expression of said nucleic acid cassette predominatly in a specific tissue.

10. The vector of claim 9, wherein said specific tissue is myogenic.

11. The vector of claim 1, wherein said 5' flaking region comprises a promoter, a TATA box, a Cap site and a first intron and intronlexon boundary in operable linkage for expression of said nucleic acid cassette.

12. The vector of claim 11, wherein said 5' flanking region further comprises a 5' mRNA leader sequence inserted between said promoter and said nucleic acid cassette.

13. The vector of claim 1, wherein said vector further comprises a 5'UTR sequence of a chicken skeletal α-actin gene.

14. The vector of claim 1, wherein said vector further comprises an antibiotic resistance gene.

15. A formulation for delivery and expression of a human GHRH gene in a muscle cell in vivo, said formulation comprising the vector of claim 1 and a stabilizing or transfection enhancing component selected from the group consisting of: polyvinyl pyrrolidone ("PVP"), cationic lipid and neutral-co-lipid.

16. The formulation of claim 15, wherein said stabilizing or transfection enhancing component includes about 5% PVP.

17. A cell transformed in vitro with the vector of claim 1.

18. The transformed cell of claim 17, wherein said cell is a myoblast.

19. A method for tranfection of a cell in vitro, comprising the step of contacting said cell with the vector of claim 1 for sufficient time to transfect said cell.

20. The method of claim 19, wherein transfection of said cell is performed ex vivo, further comprising the steps of cotransfecting said vector with a selectable marker and selecting the transformed cells.

21. A method for transfection of a muscle cell in vivo, comprising the step of administering directly to said cell the vector of claim 1 for sufficient time to transfect said cell.

22. The method of claim 21, wherein said contacting is performed in the presence of an about 5% PVP solution.

23. A method for delivery and expression of a GHRH gene in a plurality of muscle cells, comprising the steps of:
    (a) administering directly to said plurality of muscle cells the vector of claim 1; and
    (b) incubating said plurality of muscle cells under conditions that allow the expression of the nucleotide sequence encoding the GHRH in said vector.

24. The method of claim 23, wherein said cells are human cells.

25. The method of claim 24, wherein said transfecting is performed in the presence of an about 5% PVP solution.

26. The vector of claim 1, wherein said vector comprises a nucleotide sequence which is the same as the nucleotide sequence of plasmid pSK-GHRH.

* * * * *

SEQUENCE LISTING

```
<160> NUMBER OF SEQ ID NOS: 15

<210> SEQ ID NO 1
<211> LENGTH: 228
<212> TYPE: DNA
<213> ORGANISM: Homo sapiens

<400> SEQUENCE: 1
atggtgctct gggtgttctt ctttgtgatc ctcaccctca gcaacagctc ccactgctcc      60
ccacctcccc ctttgaccct caggatgcgg cggtatgcag atgccatctt caccaacagc    120
taccggaagg tgctgggcca gctgtccgcc cgcaagctgc tccaggacat catgagcagg    180
cagcagggag agagcaacca agagcgagga gcaagggcac ggctttaa                 228

<210> SEQ ID NO 2
<211> LENGTH: 228
<212> TYPE: DNA
<213> ORGANISM: Artificial sequence
<220> FEATURE:
<223> OTHER INFORMATION: Codon optimized sequence of hGHRH for
      expression in human cells

<400> SEQUENCE: 2
atggtgctgt gggtgttctt cttcgtgatc ctgaccctga gcaacagcag ccactgcagc      60
cccccccccc ccctgaccct gcgcatgcgc cgctacgccg acgccatctt caccaacagc    120
taccgcaagg tgctgggcca gctgagcgcc cgcaagctgc tgcaggacat catgagccgc    180
cagcagggcg agagcaacca ggagcgcggc gcccgcgccc gctgtga                  228

<210> SEQ ID NO 3
<211> LENGTH: 10
<212> TYPE: DNA
<213> ORGANISM: Artificial sequence
<220> FEATURE:
<223> OTHER INFORMATION: The inner core of the serum response element
<221> NAME/KEY: misc_feature
<222> LOCATION: (3)..(8)
<223> OTHER INFORMATION: The letter "w" stands for a or t

<400> SEQUENCE: 3 ccwwwwwwgg                                                             10

<210> SEQ ID NO 4
<211> LENGTH: 1441
<212> TYPE: DNA
<213> ORGANISM: Artificial sequence
<220> FEATURE:
<223> OTHER INFORMATION: Plasmid SK-GHRH NotI/SalI fragment, including
      SK promotor, GHRH cDNA, hGH3'

<400> SEQUENCE: 4
ggccgctctt actgcctgcc ccctgcctgg cacagcccgt acctggccgc acgctccctc      60
```

-continued

```
acaggtgaag ctcgaaaact ccgtccccgt aaggagcccc gctgccccccc gaggcctcct      120 ccctcacgcc tcgctgcgct cccggctccc gcacggccct gggagaggcc cccaccgctt      180
cgtccttaac gggcccggcg gtgccggggg attattttcg gcctctcggc cggggggcc       240 cggcagacgc tccttatacg gcccggcctc gctcacctgg gccgcggcca ggagcgcctt      300
ctttgggcag cgcggggccg gggccgcgcc gggcccgaca cccaaatatg gcgacggccg      360
gggccgcatt cctgggggcc gggcggtgct cccgcccgcc tcgataaaag gctccggggc      420
cggcggcggc ccacgagcta cccggaggag cgggaggcgt ctctgcctag aactagtgga      480
tcccaaggcc caactccccg aaccactcag gtcctgtgg acagctcacc tagctgccat       540
ggtgctctgg gtgttcttct ttgtgatcct caccctcagc aacagctccc actgctcccc      600 acctcccct ttgaccctca ggatgcggcg gtatgcagat gccatcttca ccaacagcta      660
ccggaaggtg ctgggccagc tgtccgcccg caagctgctc caggacatca tgagcaggca      720
gcagggagag agcaaccaag agcgaggagc aagggcacgg ctttaatgac tgcaggaatt      780
cgatatcaag cttatcgagg gtggcatccc tgtgaccccct ccccagtgcc tctcctggcc      840
ctggaagttg ccactccagt gcccaccagc cttgtcctaa taaaattaag ttgcatcatt      900
ttgtctgact aggtgtcctt ctataatatt atggggtgga gggggtggt atggagcaag       960 gggcccaagt tgggaagaca acctgtaggg cctgcgggt ctattcggga accaagctgg      1020
agtgcagtgg cacaatcttg gctcactgca atctccgcct cctgggttca agcgattctc     1080
ctgcctcagc ctcccgagtt gttgggattc aggcatgca tgaccaggct cagctaattt     1140
ttgttttttt ggtagagacg gggtttcacc atattggcca ggctggtctc caactcctaa     1200
tctcaggtga tctacccacc ttggcctccc aaattgctgg gattacaggc gtgaaccact     1260
gctcccttcc ctgtccttct gattttaaaa taactatacc agcaggagga cgtccagaca     1320
cagcataggc tacctgccat ggcccaaccg gtgggacatt tgagttgctt gcttggcact     1380
gtcctctcat gcgttgggtc cactcagtag atgcctgttg aattcaagct tatcgatacc     1440
g                                                                    1441
```

<210> SEQ ID NO 5
<211> LENGTH: 44
<212> TYPE: PRT
<213> ORGANISM: Bos taurus GHRH

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala Lys Val Arg Leu
        35                  40

<210> SEQ ID NO 6
<211> LENGTH: 44
<212> TYPE: PRT
<213> ORGANISM: Sus scrofa GHRH

<400> SEQUENCE: 6

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

```
Glu Arg Asn Gln Glu Gln Gly Ala Arg Val Arg Leu
        35                  40

<210> SEQ ID NO 7
<211> LENGTH: 44
<212> TYPE: PRT
<213> ORGANISM: Ovis Aries GHRH

<400> SEQUENCE: 7

Tyr Ala Asp Ala Ile Phe Thr Asn Ser Tyr Arg Lys Ile Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala Lys Val Arg Leu
        35                  40

<210> SEQ ID NO 8
<211> LENGTH: 42
<212> TYPE: PRT
<213> ORGANISM: Mus musculus GHRH

<400> SEQUENCE: 8

His Val Asp Ala Ile Phe Thr Thr Asn Tyr Arg Lys Leu Leu Ser Gln
1               5                   10                  15

Leu Tyr Ala Arg Lys Val Ile Gln Asp Ile Met Asn Lys Gln Gly Glu
            20                  25                  30

Arg Ile Gln Glu Gln Arg Ala Arg Leu Ser
        35                  40

<210> SEQ ID NO 9
<211> LENGTH: 44
<212> TYPE: PRT
<213> ORGANISM: Capra hircus GHRH

<400> SEQUENCE: 9

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala Lys Val Arg Leu
        35                  40

<210> SEQ ID NO 10
<211> LENGTH: 40
<212> TYPE: PRT
<213> ORGANISM: Homo sapiens GHRH

<400> SEQUENCE: 10

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala
        35                  40

<210> SEQ ID NO 11
<211> LENGTH: 44
<212> TYPE: PRT
<213> ORGANISM: Artificial sequence
<220> FEATURE:
<223> OTHER INFORMATION: Mus/porcine chimeric growth hormone releasing
      hormone sequence
```

-continued

```
<400> SEQUENCE: 11

His Val Asp Ala Ile Phe Thr Thr Asn Tyr Arg Lys Leu Leu Ser Gln
1               5                   10                  15
Leu Ser Ala Arg Lys Leu Leu Gln Asp Ile Met Ser Arg Gln Gln Gly
            20                  25                  30
Glu Arg Asn Gln Glu Gln Gly Ala Arg Val Arg Leu
        35                  40

<210> SEQ ID NO 12
<211> LENGTH: 19
<212> TYPE: DNA
<213> ORGANISM: Artificial sequence
<220> FEATURE:
<223> OTHER INFORMATION: Oligonucleotide primer (sense sequence) used to
      amplify a 254 bp fragment of pSK-GHRH cDNA

<400> SEQUENCE: 12
tggtgctctg ggtgttctt                                              19

<210> SEQ ID NO 13
<211> LENGTH: 20
<212> TYPE: DNA
<213> ORGANISM: Artificial sequence
<220> FEATURE:
<223> OTHER INFORMATION: Oligonucleotide primer (antisense sequence)
      used to amplify a 254 bp fragment of pSK-GHRH cDNA

<400> SEQUENCE: 13
gcttgatatc gaattcctgc                                             20

<210> SEQ ID NO 14
<211> LENGTH: 20
<212> TYPE: DNA
<213> ORGANISM: Artificial sequence
<220> FEATURE:
<223> OTHER INFORMATION: Oligonucleotide primer (sense sequence) used to
      amplify a 497 bp control fragment of mus cytoskeletal B-action
      cDNA

<400> SEQUENCE: 14
tcagaaggac tcctatgtgg                                             20

<210> SEQ ID NO 15
<211> LENGTH: 20
<212> TYPE: DNA
<213> ORGANISM: Artificial sequence
<220> FEATURE:
<223> OTHER INFORMATION: Oligonucleotide primer (antisense sequence)
      used to amplify a 497 bp control fragment of mus cytoskeletal
      B-action cDNA

<400> SEQUENCE: 15
tctctttgat gtcacgcacg                                             20
```